(12) United States Patent
Johnson et al.

(10) Patent No.: US 8,119,657 B2
(45) Date of Patent: Feb. 21, 2012

(54) ENANTIOMERIC COMPOSITIONS OF 2-AMINO-1-(2-ISOPROPYLPYRAZOLO[1,5-α]PYRIDIN-3-YL)PROPAN-1-ONE AND RELATED METHODS

(75) Inventors: Kirk W. Johnson, Moraga, CA (US); Matthew I. Gross, Vallejo, CA (US); Federico C. A. Gaeta, Mountain View, CA (US)

(73) Assignee: MediciNova, Inc., San Diego, CA (US)

( * ) Notice: Subject to any disclaimer, the term of this patent is extended or adjusted under 35 U.S.C. 154(b) by 0 days.

(21) Appl. No.: 12/820,993

(22) Filed: Jun. 22, 2010

(65) Prior Publication Data

US 2010/0324082 A1    Dec. 23, 2010

Related U.S. Application Data

(60) Provisional application No. 61/219,664, filed on Jun. 23, 2009.

(51) Int. Cl.
*A61K 31/44* (2006.01)
*C07D 491/02* (2006.01)
*C07D 498/02* (2006.01)

(52) U.S. Cl. .................... 514/300; 546/121
(58) Field of Classification Search ............... 514/300; 546/121
See application file for complete search history.

(56) References Cited

U.S. PATENT DOCUMENTS

| 4,097,483 | A | 6/1978 | Irikura |
| 7,585,875 | B2 * | 9/2009 | Gaeta et al. ............. 514/300 |
| 2007/0015924 | A1 | 1/2007 | Jung et al. |
| 2008/0070912 | A1 | 3/2008 | Gaeta et al. |
| 2009/0062330 | A1 | 3/2009 | Kalafer et al. |
| 2009/0318437 | A1 * | 12/2009 | Gaeta et al. ............. 514/233.2 |

FOREIGN PATENT DOCUMENTS

| WO | 2007146087 | * 12/2007 |
| WO | WO-2007/142924 | 12/2007 |

OTHER PUBLICATIONS

"Remington: The Science & Practice of Pharmacy", 19th ed., Williams & Williams, (1995).
Alisky, et al., "Gene Therapy for Amyotgrophic Lateral Sclerosis and Other Motor Neuron Diseases", Human Gene Therapy, (2000) 11:2315-2329.
Bennett et al., "A peripheral mononeuropathy in rat that produces disorders of pain sensation like those seen in man", Pain 1988; 33(1):87-107.
Burger's Medicinal Chemistry and Drug Discovery 6th ed. vol. 1-6, (Wiley, 2001) and Design and Application of Prodrugs, edited by Donald J. Abraham(Harwood Academic Publishers GmbH, 1985).
Chiang, "New Developments in Cancer Pain Therapy", Acta Anaesthesiol. Sin. (2000) 38:31-36.

Davidson et al., "A model system for in vivo gene transfer into the central nervous system using an adenoviral vector" Nature Genetics, vol. 3, Mar. 1993, pp. 219-223.
Davidson et al., "Recombinant adeno-associated virus type 2, 4, and 5 vectors: Transduction of variant cell types and regions in the mammalian central nervous system" PNAS, Mar. 28, 2000, vol. 97, No. 7, pp. 3428-3432.
Duplantier et al., "Biarylcarboxylic Acids and -amides: Inhibition of Phosphodiesterase Type IV versus [3H]Rolipram Binding Activity and Their Relationship to Emetic Behavior in the Ferret", J Med Chem Jan. 5, 1996;39(1):120-5.
Greene's Protective Groups in Organic Synthesis, 4th ed., Wuts, P. G. M., and Greene, T. W., Wiley Interscience, 2007, chapter 7.
Handbook of Pharmaceutical Excipients, 5th ed., Rowe, R. et al., eds., American Pharmaceutical Association, 2005.
Handbook of Pharmaceutical Salts: Properties, Selection and Use, Stahl, P. H. and Wermuth, C.G. (Eds.), Wiley-VCH, (2002).
Handbook of Reagents for Organic Synthesis: Chiral reagents for asymmetric synthesis, L. Paquette, Ed., Wiley and Sons, 2003.
Jain, K.K., "An evaluation of intrathecal ziconotide for the treatment of chronic pain", Expert Opinion on Investigational Drugs,(2000) 9:2403-2410.
Jeffery et al., "The Preparation and Characterization of Poly(lactide-co-glycolide) Microparticles. II. The Entrapment of a Model Protein Using a (Water-in-Oil)-in-Water Emulsion Solvent Evaporation Technique", Pharmaceutical Research, vol. 10, No. 3, (1993), pp. 362-368.
Kibbe, A.H., Handbook of Pharmaceutical Excipients, 3rd Edition, American Pharmaceutical Association, Washington, D.C., 2000.
Ledeboer et al., "The glial modulatory drug AV411 attenuates mechanical allodynia in rat models of neuropathic pain" Neuron Glia Biology, (2006), 2, pp. 279-291.
McGee et al., "The encapsulation of a model protein in poly (D, L lactide-co-glycolide) microparticles of various sizes: an evaluation of process reproducibilitiy", Journal of Microencapsulation, vol. 14, No. 6 (1997).
Search Report and Written Opinion mailed Aug. 31, 2010 in International Appln. No. PCT/US10/039530.
Stein et al., "Systemic and Central Nervous System Correction of Lysosomal Storage in Mucopolysaccharidosis Type VII Mice" Journal of Virology, Apr. 1999, vol. 73, No. 4.
The "Physician's Desk Reference", 52nd ed., Medical Economics, Montvale, NJ (1998).
Wheeler-Aceto et al., "Standardization of the rat paw formalin test for the evaluation of analgesics", (Psychopharmacology, 104, p. 35-44, (1991)).

* cited by examiner

*Primary Examiner* — Janet Andres
*Assistant Examiner* — Niloofar Rahmani
(74) *Attorney, Agent, or Firm* — Gilberto M. Villacorta; Sunit Talapatra; Foley & Lardner LLP

(57) ABSTRACT

Enantiomerically pure (S)-2-amino-1-(2-isopropylpyrazolo [1,5-a]pyridin-3-yl)propan-1-one, (S)-AV1013, is a candidate therapeutic for treating neuropathic pain, addiction behavior and drug withdrawal symptoms. Also described are methods for preparing and using (S)-AV1013, its pharmaceutically acceptable salts as well as pharmaceutically acceptable formulations of the same.

9 Claims, 8 Drawing Sheets

ENANTIOMERIC COMPOSITIONS OF 2-AMINO-1-(2-ISOPROPYLPYRAZOLO[1,5-α]PYRIDIN-3-YL)PROPAN-1-ONE AND RELATED METHODS

CROSS REFERENCE TO RELATED APPLICATIONS

This application claims the benefit of priority of U.S. Provisional Application No. 61/219,664 filed on Jun. 23, 2009. The entire disclosure of which is incorporated herein by reference.

FIELD

The present application is directed to methods for making enantiomerically pure (S)-2-amino-1-(2-isopropylpyrazolo [1,5-a]pyridin-3-yl)propan-1-one or its pharmaceutically acceptable salts, as well as to compositions comprising the same. Also described are methods for using the inventive compositions to treat inflammation, pain and drug withdrawal symptoms.

BACKGROUND

Substituted pyrazolo[1,5-a]pyridine compounds are described in U.S. Patent Publication No. US 2008/0070912. Numerous structures, synthetic methodologies, in vitro and in vivo assay results are also described.

SUMMARY

The present disclosure is based at least in part upon the Applicants' surprising discovery that there is a preference in vivo for the (S)-enantiomer of 2-amino-1-(2-isopropylpyrazolo[1,5-a]pyridin-3-yl)propan-1-one. Thus, while in vitro data suggests only very slight differences in bioactivity between the two enantiomers, the Applicants have discovered a surprising and notable in vivo preference for the (S)-enantiomer, as indicated by pharmacological parameters, such as, the level of (S)-enantiomer in circulating blood. Moreover, significantly enhanced potency of the (S)-enantiomer was observed in a well-established animal model for treating neuropathic pain.

In one embodiment, therefore, the present disclosure provides enantiomerically pure (S)-2-amino-1-(2-isopropylpyrazolo[1,5-a]pyridin-3-yl)propan-1-one (Compound (S)-1013) or a pharmaceutically acceptable salt or prodrug thereof. The structure of (S)-2-amino-1-(2-isopropylpyrazolo[1,5-a]pyridin-3-yl)propan-1-one is shown below, where the amino group may also be in the form of a pharmaceutically acceptable acid addition salt (i.e., where the pendant amino group is protonated and accompanied by a suitable counter ion).

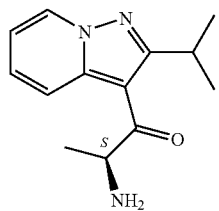

For example, pharmaceutically acceptable acid salt forms of the inventive compounds include salts prepared by reacting the amine group with inorganic acids, to give the corresponding ammonium chloride, sulfate, phosphate, bromide, and nitrate salts, or salts prepared with an organic carboxylic or sulfonic acid, such as ammonium malate, maleate, fumarate, tartrate, succinate, ethylsuccinate, citrate, acetate, lactate, methanesulfonate, benzoate, ascorbate, para-toluenesulfonate, pamoate, salicylate, and stearate, as well as estolate, gluceptate and lactobionate salts.

In a particular exemplary embodiment, the pharmaceutically acceptable acid salt is a salt of an inorganic acid such as, a salt with hydrochloric acid to give the corresponding (S)-2-amino-1-(2-isopropylpyrazolo[1,5-a]pyridin-3-yl)propan-1-one hydrochloride.

The present invention also encompasses a composition comprising a single enantiomer of 2-amino-1-(2-isopropylpyrazolo[1,5-a]pyridin-3-yl)propan-1-one, for example, a composition comprising (S)-2-Amino-1-(2-isopropylpyrazolo[1,5-a]pyridin-3-yl)propan-1-one or its pharmaceutically acceptable salt. According to one aspect of the invention, therefore, the enantiomeric purity of (S)-2-amino-1-(2-isopropylpyrazolo[1,5-a]pyridin-3-yl)propan-1-one in the inventive composition is in a range from about 90% to 99.9%, suitably about 94% (i.e., 94% enantiomeric excess) or greater.

The terms "chiral purity" and "enantiomeric purity" are used interchangeably throughout the specification and refer to a measure of the purity of a substance (enantiomer) with the undesired enantiomer being the impurity. The term "enantiomeric excess" refers to the absolute difference between the mole fraction of each enantiomers as further defined below. According to one aspect, therefore, the enantiomeric purity of (S)-2-amino-1-(2-isopropylpyrazolo[1,5-a]pyridin-3-yl)propan-1-one or its pharmaceutically acceptable salt in the inventive composition is about 90% or greater, about 91% or greater, about 92% or greater, about 93% or greater, about 94% or greater, about 95% or greater, or about 96% or greater, or about 97% or greater, or about 98% or greater, or about 99% or greater, or even about 99.9% or greater.

In yet a further embodiment, (S)-2-Amino-1-(2-isopropylpyrazolo[1,5-a]pyridin-3-yl)propan-1-one exhibits a $C_{max}$ that is at least 3-fold greater than that of the corresponding (R)-enantiomer based upon oral dosing of racemic 2-amino-1-(2-isopropylpyrazolo[1,5-a]pyridin-3-yl)propan-1-one in rats. In yet another related embodiment, (S)-2-Amino-1-(2-isopropylpyrazolo[1,5-a]pyridin-3-yl)propan-1-one exhibits a $C_{max}$ that is at least 2-fold greater than that of the corresponding (R)-enantiomer based upon oral dosing of the racemate in dogs.

In another aspect the invention is directed to a (S)-2-amino-1-(2-isopropylpyrazolo[1,5-a]pyridin-3-yl)propan-1-one or a pharmaceutically acceptable salt thereof for veterinary or human medical use in treating a condition selected from neuropathic pain, an inflammation, inflammatory pain, opioid dependence or opioid withdrawal syndrome.

Described herein, therefore, is a method for treating a mammalian subject experiencing neuropathic pain by administering to the subject a therapeutically effective amount of (S)-2-amino-1-(2-isopropylpyrazolo[1,5-a]pyridin-3-yl)propan-1-one or a pharmaceutically acceptable salt or prodrug thereof, whereby as a result of the administering, the subject experiences relief of the neuropathic pain.

In another aspect, is provided a method for treating various inflammatory syndromes in a mammalian subject, by administering to the subject suffering from an inflammatory condition a therapeutically effective amount of (S)-2-amino-1-(2-isopropylpyrazolo[1,5-a]pyridin-3-yl)propan-1-one or a pharmaceutically acceptable salt or prodrug thereof.

In yet another aspect, described is a method for treating opioid dependence or opioid withdrawal syndromes by administering to a mammalian subject suffering from opioid dependence or opioid withdrawal a therapeutically effective amount of (S)-2-amino-1-(2-isopropylpyrazolo[1,5-a]pyridin-3-yl)propan-1-one or a pharmaceutically acceptable salt [or prodrug] thereof.

While the use of AV1013 as a suitable therapeutic for treating opioid dependency and/or withdrawal syndrome is exemplified below, it should be noted that the therapeutic efficacy of AV1013 can extend to other drugs of abuse for which physical dependency and withdrawal are observed. Illustrative of drugs that invoke physical dependency and withdrawal, without limitation are marijuana, nicotine, alcohol, as well as stimulants such as cocaine, amphetamine and methamphetamine.

AV1013 like ibudilast can attenuate the symptoms of reward-behavior (craving), accompanying spontaneous withdrawal. AV1013 also reduces addiction by alleviating or reducing the inclination for relapse and the magnitude of relapse. Without being bound to a particular hypothesis, however, the present inventors believe that the efficacy of AV0103 in treating withdrawal is probably due to its structural similarity to the therapeutic agent ibudilast, used for treating pain, opioid dependency and withdrawal symptoms.

In yet another aspect, the disclosure provides a method for preparing (S)-2-amino-1-(2-isopropylpyrazolo[1,5-a]pyridin-3-yl)propan-1-one or a pharmaceutically acceptable salt [or prodrug] thereof. The method comprises the steps of (i) conducting chiral chromatography of racemic 2-N-protected-amino-1-(2-isopropylpyrazolo[1,5-a]pyridin-3-yl)propan-1-one to provide (S)-2-N-protected-amino-1-(2-isopropylpyrazolo[1,5-a]pyridin-3-yl)propan-1-one, and, (ii) removing the 2-N-amino protecting group to provide (S)-2-amino-1-(2-isopropylpyrazolo[1,5-a]pyridin-3-yl)propan-1-one or a pharmaceutically acceptable salt thereof in greater than about 95% chiral purity.

Illustrative of a chiral chromatographic method suitable for use in the inventive method is super critical fluid chromatography (SFC).

In yet another embodiment of the method, the racemic 2-N-protected-amino-1-(2-isopropylpyrazolo[1,5-a]pyridin-3-yl)propan-1-one comprises a protecting group at the 2-amino position selected from fluorenylmethyloxycarbonyl (FMOC), tert-butoxycarbonyl (BOC), benzyl carbamate, acetamide, trifluoroacetamide, benzyl amine, triphenylmethylamine (trityl), benzylideneamine, p-toluenesulfonamide (tosylamide).

In a further embodiment, the protecting group is selected from benzyl carbamate, BOC, and trifluoroacetamide.

In yet an additional aspect, provided herein is a method for preparing 2-amino-1-(2-isopropylpyrazolo[1,5-a]pyridin-3-yl)propan-1-one, comprising the steps of: (i) transforming desmethylibudilast (normethylibudilast, AV1001) into the corresponding oxime ketone (C), and (ii) hydrogenating the alpha-oximinoketonefrom step (i) to form 2-amino-1-(2-isopropylpyrazolo[1,5-a]pyridin-3-yl)propan-1-one.

In yet another aspect, described herein is a method for preparing 2-amino-1-(2-isopropylpyrazolo[1,5-a]pyridin-3-yl)propan-1-one comprising the steps of: (I) converting the keto group of desmethylibudilast (normethylibudilast, AV1001) into the corresponding oxime, nor-methylibudilast oxime (D), (ii) reacting nor-methylibudilast oxime with a tosylating agent to form the oxime tosylate (E), and (iii) transforming the oxime tosylate from step (ii) via a Neber rearrangement carried out in the presence of base to form 2-amino-1-(2-isopropylpyrazolo[1,5-a]pyridin-3-yl)propan-1-one.

In an additional embodiment, the above methods for preparing 2-amino-1-(2-isopropylpyrazolo[1,5-a]pyridin-3-yl)propan-1-one further comprise isolating (S)-2-amino-1-(2-isopropylpyrazolo[1,5-a]pyridin-3-yl)propan-1-one from racemic 2-amino-1-(2-isopropylpyrazolo[1,5-a]pyridin-3-yl)propan-1-one via chiral resolution or kinetic dynamic resolution of the corresponding acid salt.

Also described herein is (S)-2-amino-1-(2-isopropylpyrazolo[1,5-a]pyridin-3-yl)propan-1-one obtainable by any of the methods described herein.

Additional embodiments, related compositions and methods will be apparent from the following description, drawings and examples. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present disclosure.

These and other objects and features will become more fully apparent when read in conjunction with the following detailed description.

BRIEF DESCRIPTION OF THE DRAWINGS

FIG. 3 provides a graph illustrating attenuation of mechanical allodynia observed in rats following administration of individual isomers of AV1013 in a rat chronic constriction injury model of neuropathic pain as described in detail in Example 3.

DETAILED DESCRIPTION

Figure 1:
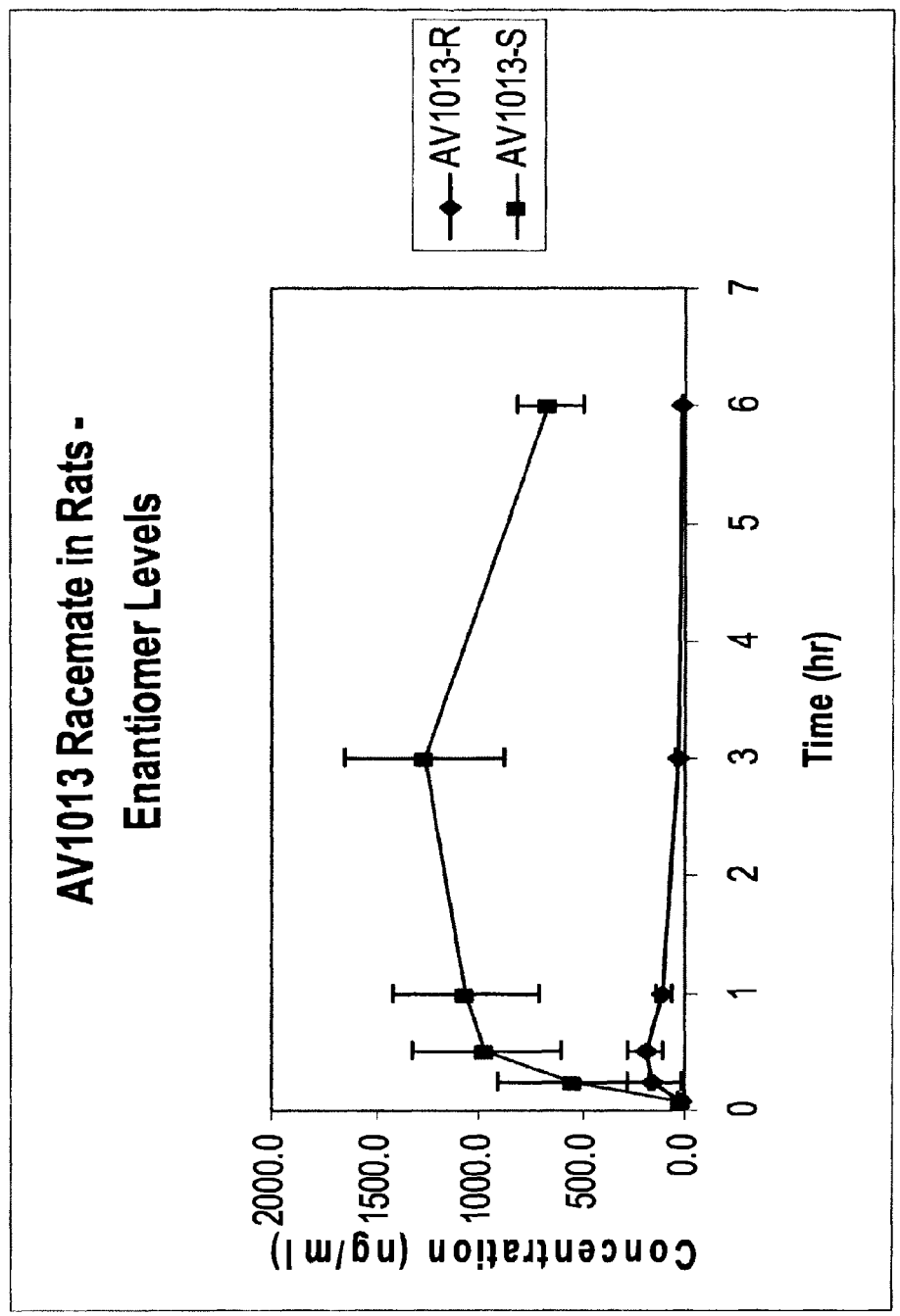
FIG. 1 is a graph illustrating plasma concentrations of each of (R)-AV1013 and (S)-AV1013 over time upon dosing racemic AV1013 orally in rats as described in Example 2. As shown in this figure, plasma concentration levels of the (S)-enantiomer of AV1013 are higher than those of the (R)-enantiomer over a period of 6 hours.

The present invention now will be described more fully hereinafter. This invention may, however, be embodied in many different forms and should not be construed as limited to the embodiments set forth herein; rather, these embodiments are provided so that this disclosure will be thorough, and will fully convey the scope of the invention to those skilled in the art.

All publications, patents and patent applications cited herein, whether supra or infra, are hereby incorporated by reference in their entirety.

DEFINITIONS

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

The following terminology will be used in accordance with the definitions described below.

"Pharmaceutically acceptable excipient or carrier" refers to an excipient that may optionally be included in the compositions of the invention and that causes no significant adverse toxicological effects to the patient. Suitable excipients may be found in, e.g., Handbook of Pharmaceutical Excipients, 5$^{th}$ ed., Rowe, R. et al., eds., American Pharmaceutical Association, 2005.

"Pharmaceutically acceptable salt" includes, but is not limited to, non-toxic salts, in the instant case, typically acid addition salts such as those prepared with inorganic acids, such as hydrochloride, sulfate, phosphate, formate, perchlorate, diphosphate, hydrobromide, and nitrate salts, or salts prepared with an organic carboxylic or sulfonic acid, such as malate, maleate, fumarate, tartrate, succinate, ethylsuccinate, citrate, acetate, lactate, methanesulfonate, benzoate, ascorbate, para-toluenesulfonate, pamoate, salicylate and stearate, as well as estolate, gluceptate and lactobionate salts. Pharmaceutically acceptable salts are described in *Handbook of Pharmaceutical Salts: Properties, Selection and Use*, Stahl, P. H. and Wermuth, C. G. (Eds.), Wiley-VCH.

"Chiral chromatography" refers to chromatographic separation of chiral substances such as enantiomers. Enantiomeric separations are achieved in chiral chromatography by the judicious use of chiral phases. The mobile phase can be a gas or liquid giving rise to chiral gas chromatography and chiral liquid chromatography. Chiral selectivity is usually achieved by employing chiral stationary phases, although, in chiral liquid chromatography, chiral mobile phases have been successfully employed. For any chiral separation, the stationary phase must be chosen so that the spatial arrangement of its composite atoms increases the probability or proximity of interaction differing significantly between the two enantiomers to be separated.

"Chiral purity" or "enantiomeric purity" are used interchangeably and refer to enantiomeric excess or ee. For example, the chiral purity of enantiomer, E$^-$, is defined as the absolute difference between the mole fraction of each enantiomer, where the sum of the mole fractions of two enantiomers, E$^-$ and E$^+$ is defined as 1. Typically, enantiomeric excess is expressed as a percent where:

$$ee=[|R-S|\div(R+S)]\times 100.$$

"Substantially" or "essentially" means nearly totally or completely, for instance, about 95% or greater of some given quantity.

"Majority" as used herein refers to more than half of some given quantity.

"Optional" or "optionally" means that the subsequently described circumstance may or may not occur, so that the description includes instances where the circumstance occurs and instances where it does not.

By "pathological pain" is meant any pain resulting from a pathology, such as from functional disturbances and/or pathological changes, lesions, burns, injuries, and the like. One form of pathological pain is "neuropathic pain" which is pain thought to initially result from nerve damage but extended or exacerbated by other mechanisms including glial cell activation. Examples of pathological pain include, but are not limited to, thermal or mechanical hyperalgesia, thermal or mechanical allodynia, diabetic pain, pain arising from irritable bowel or other internal organ disorders, endometriosis pain, phantom limb pain, complex regional pain syndromes, fibromyalgia, low back pain, cancer pain, pain arising from infection, inflammation or trauma to peripheral nerves or the central nervous system, spinal cord injury pain, chemotherapy-induced neuropathic pain, multiple sclerosis pain, entrapment pain, and the like.

"Hyperalgesia" means an abnormally increased pain sense, such as pain that results from an excessive sensitiveness or sensitivity. Examples of hyperalgesia include but are not limited to cold or heat hyperalgesia.

"Hypalgesia" (or "hypoalgesia") means the decreased pain sense.

"Allodynia" means pain sensations that result from normally non-noxious stimulus to the skin or body surface. Examples of allodynia include, but are not limited to, cold or heat allodynia, tactile or mechanical allodynia, and the like.

"Nociception" is defined herein as pain sense. "Nociceptor" herein refers to a structure that mediates nociception. The nociception may be the result of a physical stimulus, such as, mechanical, electrical, thermal, or a chemical stimulus. Nociceptors are present in virtually all tissues of the body.

"Analgesia" is defined herein as the relief of pain without the loss of consciousness. An "analgesic" is an agent or drug useful for relieving pain, again, without the loss of consciousness.

The term "central nervous system" or "CNS" includes all cells and tissue of the brain and spinal cord of a vertebrate. Thus, the term includes, but is not limited to, neuronal cells, glial cells, astrocytes, cerebrospinal fluid (CSF), interstitial spaces and the like.

"Glial cells" refer to various cells of the CNS also known as microglia, astrocytes, and oligodendrocytes.

The terms "subject", "individual" or "patient" are used interchangeably herein and refer to a vertebrate, preferably a mammal. Mammals include, but are not limited to, murines, rodents, simians, humans, farm animals, sport animals and pets. Such subjects are typically suffering from or prone to a condition that can be prevented or treated by administration of a compound of the invention.

The term "about", particularly in reference to a given quantity, is meant to encompass deviations of plus or minus five percent.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). Prodrugs can typically be prepared using well-known methods, such as those described by BURGER'S MEDICINAL CHEMISTRY AND DRUG DISCOVERY 6th ed. (Wiley, 2001) and DESIGN AND APPLICATION OF PRODRUGS (Harwood Academic Publishers GmbH, 1985).

"Treatment" or "treating" of a particular condition includes: (1) preventing such a condition, i.e. causing the condition not to develop, or to occur with less intensity or to a lesser degree in a subject that may be exposed to or predisposed to the condition but does not yet experience or display the condition, (2) inhibiting the condition, i.e., arresting the development or reversing the condition.

The term "addiction" is defined herein as compulsively using a drug or performing a behavior repeatedly that increases extracellular dopamine concentrations in the nucleus accumbens. An addiction may be to a drug including, but not limited to, psychostimulants, narcotic analgesics, alcohols and addictive alkaloids such as nicotine, cannabinoids, or combinations thereof.

A subject suffering from an addiction experiences addiction-related behavior, cravings to use a substance in the case of a drug addiction or overwhelming urges to repeat a behavior in the case of a behavioral addiction, the inability to stop drug use or compulsive behavior in spite of undesired consequences (e.g., negative impacts on health, personal relationships, and finances, unemployment, or imprisonment), reward/incentive effects associated with dopamine release, and dependency, or any combination thereof.

Addiction-related behavior in reference to a drug addiction includes behavior resulting from compulsive use of a drug characterized by dependency on the substance. Symptomatic of the behavior is (i) overwhelming involvement with the use of the drug, (ii) the securing of its supply, and (iii) a high probability of relapse after withdrawal.

By "water soluble" is meant a compound that is soluble in water to an extent of at least 10 milligrams per milliliter in water at 25° C. and a pH 7.0.

By "Inflammation" is meant the dynamic complex of cytologic and chemical reactions that occur in affected blood vessels and adjacent tissues in response to an injury or abnormal stimulation caused by a physical, chemical, or biologic agent, including: (1) the local reactions and resulting morphologic changes, (2) the destruction or removal of the injurious material, (3) the responses that lead to repair and healing. Common signs of inflammation are: redness; heat (or warmth); swelling; and pain; and inhibited or lost function. All of the signs may be observed in certain instances, but no one of them is necessarily always present.

"Inflammatory pain" refers to the state of pain hypersensitivity that accommodates inflammation.

OVERVIEW

Pharmacological studies of substituted pyrazolo[1,5-a]pyridine compounds, have lead to the unexpected discovery that 2-amino-1-(2-isopropylpyrazolo[1,5-a]pyridin-3-yl)propan-1-one (Compound AV1013, also referred to herein as AV1013) exhibits enantioselective pharmacokinetics in vivo. Specifically, a significantly higher plasma concentration of the S-enantiomer was detected in vivo upon dosing two different mammalian species with racemic 2-amino-1-(2-isopropylpyrazolo[1,5-a]pyridin-3-yl)propan-1-one. Additional studies have shown that while the parent racemate shows significant in vivo activity in a rat model of neuropathic pain, the R-enantiomer, however, demonstrates little or no in vivo activity. Taken together, these results indicate that the in vivo activity shown by the racemate is predominantly from the (S)-enantiomer. Data in support of the surprising advantages and properties of (S)-2-amino-1-(2-isopropylpyrazolo[1,5-a]pyridin-3-yl)propan-1-one and preparation of the subject (S)-enantiomer are provided in the accompanying Examples.

Figure 6:
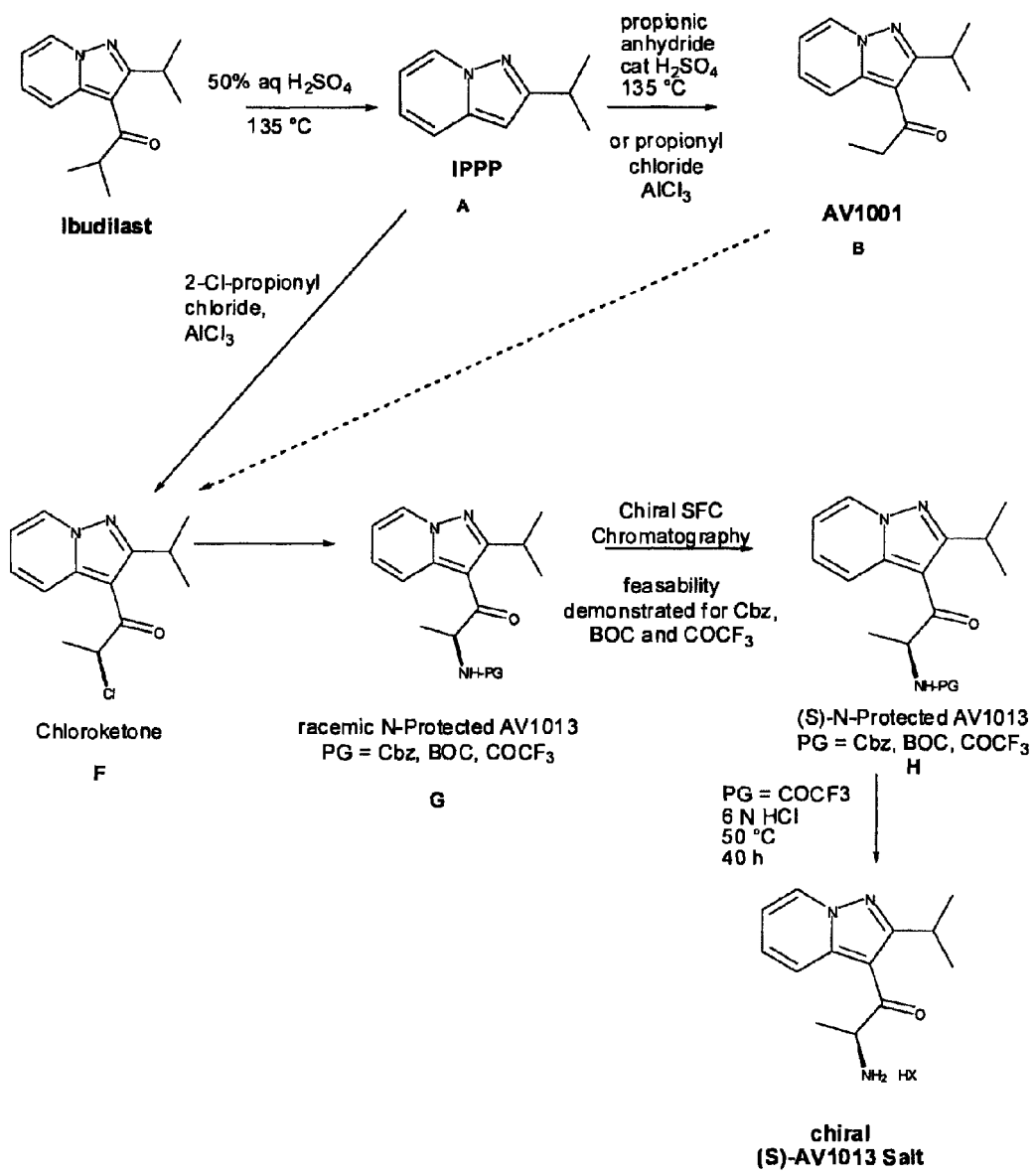
FIG. 6 is a synthetic reaction scheme illustrating one approach for preparing (S)-AV1013; the approach employs chiral chromatography of an N-protected form of the racemate as described in detail in Example 1.
Figure 7:
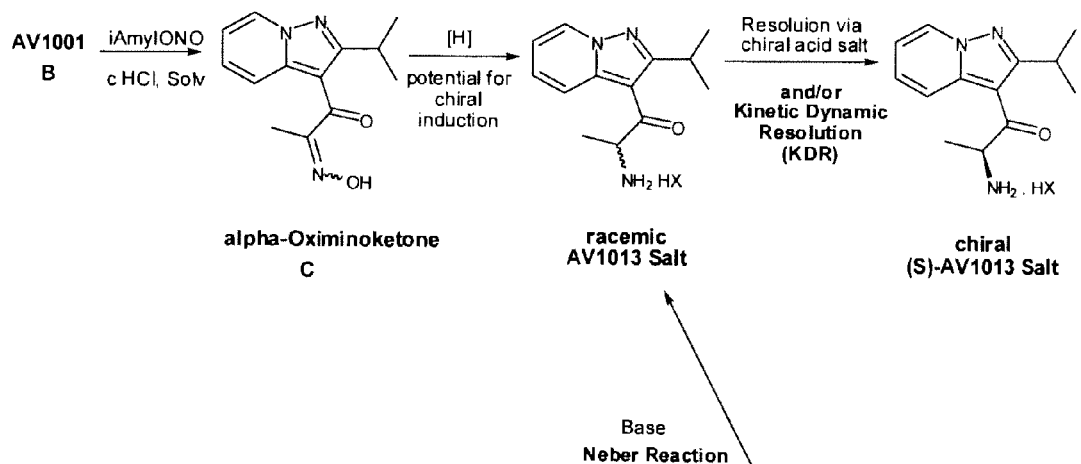
FIG. 7 demonstrates additional reaction schemes for synthesizing (S)-AV1013.
Figure 7:
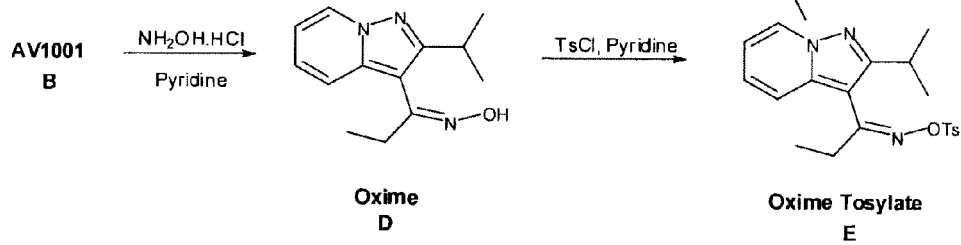

Preparation of 2-amino-1-(2-isopropylpyrazolo[1,5-a]pyridin-3-yl)propan-1-one (Compound 1013) Racemate and Single Isomers Thereof The present invention provides methodologies for obtaining optically pure (S)-2-amino-1-(2-isopropylpyrazolo[1,5-a]pyridin-3-yl)propan-1-one (Compound (S)-1013, used interchangeably herein with the designation (S)-AV1013). For example, (S)-1013 can be obtained using asymmetric synthesis, or by chiral resolution of the racemate. FIGS. 6 and 7 illustrate these synthetic approaches that are further described in the the working examples.

According to one approach, therefore, the desired S-enantiomer of AV1013 is prepared by chiral resolution of the corresponding racemic mixture. As shown in FIG. 6, and described in the Example 1 below, synthesis of AV1013 involves several steps. The first step involves the synthesis of 2-chloro-nor-methylibudilast using either ibudilast (2-methyl-1-(2-isopropylpyrazolo[1,5-a]pyridin-3-yl)propan-1-one) or the corresponding 3-carboxylic acid (2-isopropyl-pyrazolo[1,5-a]pyridin-3-carboxylic acid, ibudilast acid) as the starting material. Thus, reacting ibudilast with an aqueous solution of a strong inorganic acid, for example, 50% aqueous sulfuric gave isopropylpyrazolo[1,5-a]pyridine (IPPP) following a loss of its 3-ring substituent (2-methyl-propan-1-one). Alternatively IPPP is obtained via the decarboxylation of 2-isopropyl-pyrazolo[1,5-a]pyridine-3-carboxylic acid under acidic conditions. See, Example 1, method 2, step 1.

The second step in the synthesis of AV1013 involves reacting the intermediate (IPPP), with 2-chloro-propan-1-one under Friedel-Craft conditions to synthesize the corresponding chloroketone. Thus, reaction of isopropylpyrazolo[1,5-a]pyridine (IPPP) with 2-chloropropionyl chloride in the presence of aluminum chloride (Example 1, Step 2), gave 2-chloro-1-(2-isopropylpyrazolo[1,5-a]pyridin-3-yl)propan-1-one (i.e., 2-chloro-desmethylibudilast). In an alternate strategy as described in Example 8, IPPP is allowed to react with propanoyl chloride under Friedel-Crafts acylation conditions to give desmethylibudilast. It should be noted that the terms desmethylibudilast and Nor-methyl ibudilast are used interchangeably throughout the specification. The obtained Nor-methyl ibudilast is then converted to the corresponding alpha-chloroketone (2-chloro-desmethylibudilast), by techniques known in the chemical art, for example, via chlorination.

As described in the working examples, 2-chloro-desmethylibudilast can be converted to the corresponding racemic N-protected 2-amino-1-(2-isopropylpyrazolo[1,5-a]pyridin-3-yl)propan-1-one by reaction with a suitably protected amine, or 2-chloro-desmethylibudilast can be reacted with liquid ammonia to obtain racemic AV1013 (2-amino-1-(2-isopropylpyrazolo[1,5-a]pyridin-3-yl)propan-1-one), whose amino group is subsequently protected using methods known in the chemical art.

The present inventors found that chiral chromatographic resolution of the racemate of AV1013 is greatly facilitated when the N-protected racemate of AV1013 is used rather than racemic AV1013 or its hydrochloride salt. Without ascribing to any particular theory, the present inventors believe that the facile separation of enantiomers using the N-protected racemate of AV1013 is probably due to the greater stability of the racemate as well as the separate enantiomers in protected form. For example, the inventors found that (S)-AV1013 free base is unstable and racemizes in solution. Unstability also stems from the ability of the free base to self condense. Because self-condensation is promoted in concentrated solutions, it is desirable to avoid highly concentrated solutions of the free base form of optically active AV1013. Likewise, the free base form of racemic AV1013 or its hydrochloride salt are also unstable, precluding their use as precursors to obtaining (S)-AV1013 as a free base or its hydrochloride salt in high yield and/or high purity.

These observations have prompted the development of synthetic methodologies that directly result in the formation of racemic N-protected AV1013. According to one such methodology, 2-chloro-desmethylibudilast was made to react with a suitably protected amine to obtain racemic N-protected AV1013. The desired (S)-enantiomer is obtained from the racemate by chiral chromatographic resolution of the racemic mixture as further described below. Any amine protecting group known in the chemical art can be used. For a review on protecting groups and their use in chemical synthesis, see, Greene's Protecting Groups in Organic Synthesis, 4$^{th}$ ed., Wuts, P. G. M., and Greene, T. W., Wiley Interscience, 2007, chapter 7). Exemplary suitable amine protecting groups without limitation include Fmoc, BOC, benzyl carbamate, acetamide, trifluoroacetamide, benzyl amine, triphenylmethylamine (trityl), benzylideneamine, p-toluenesulfonamide (tosylamide). Of these, the benzyl carbamate, BOC, and trifluoroacetamide groups are particularly favored for synthesizing AV1013. For example, the inventors found that trifluoroacetamide protecting group affords the most versatility during synthesis of (S)-AV1013 by allowing high throughput chiral separation, ease of cleavage, and shortest overall synthetic sequence. Moreover, use of trifluoroacetamide protecting group allowed the synthesis of protected AV1013 in high yield and chemical purity, that is, without the formation of side products commonly associated with the use of other protecting groups.

Racemic AV1013 synthesized according to the methodologies described above is then resolved to obtain the desired N-protected (S)-enantiomer of AV1013. In one embodiment, therefore, the present invention teaches the use of chiral chromatographic techniques to separate the desired (S)-enantiomer from the (R)-enantiomer. Suitable chiral separation methods include capillary electrophoresis, chiral chromatography, enzymatic methods, and kinetic dynamic resolution. Chiral chromatographic methods that may be employed in accordance with an aspect of this invention, include chiral high pressure liquid chromatography (HPLC), chiral gas chromatography (GC), chiral supercritical fluid chromatography (SFC), or crystallization. Example 1 describes the use of chiral SFC in resolving racemic AV1013. SFC is a form of normal phase chromatography that uses supercritical carbon dioxide as the mobile phase and a chiral support as the stationary phase. Suitable chiral stationary phases are provided in columns and include without limitation silica-based chiral-selector derivatized supports such as the Whelk-O® columns available from Regis Technologies, Inc. (Morton Grove, Ill.), derivatized polysaccharide columns such as those containing amylose and cellulose derivatized solid phases containing chiral selectors such as those available from Daicel, Inc. (e.g., CHIRALPAK® IA™, and CHIRALCEL®OD-I™).

A variety of analytical methods can be used to determiner the chiral purity of the N-protected enantiomers. Illustrative of such analytical techniques without limitation are polarimetry, NMR, calorimetry, GC/MS/MS, or any other suitable analytical method for resolving enantiomers and assessing enantiomeric purity. The desired (S)-enantiomer, 2-amino-1-(2-isopropylpyrazolo[1,5-a]pyridin-3-yl)propan-1-one, preferably in N-protected form, is recovered in an enantiomeric purity of 94% or greater, preferably 95% or greater, or 96% or greater, or 97% or greater or 98% or greater, or even 99% or greater.

The amino protecting group is removed following resolution of the N-protected enantiomers. The method of deprotection will depend, on the identity of the particular protecting group used. For instance, a benzyloxycarbonyl (Cbz), protecting group is typically removed by hydrogenolysis, a BOC (tert-butyloxycarbonyl) group is cleaved by reaction with a strong acid such as HCl or trifluoroacetic acid, and trifluoroacetyl is removed by reaction with either strong acid or strong base, or under reducing conditions. A preferred approach for removal of the trifluoroacetyl group is cleavage with strong acid such as concentrated hydrochloric acid. Cleavage of the trifluoroacetyl group with strong acid results in clean cleavage to produce the corresponding acid salt without significant degradation or loss in chiral purity (i.e., a loss in chiral purity of no more than about 1% (i.e., a compound having an initial enantiomeric purity of 98% after deprotection will possess an enantiomeric purity of 97% or more), and preferably, will exhibit no observable loss in optical purity following deprotection. See, e.g., Example 7. Due to its hygroscopic nature, (S)-AV1013.HCl is preferably handled under dry conditions (Le., with the exclusion of moisture), e.g., during filtration and/or drying or other processing steps.

As described above (S)-AV1013 racemizes slowly in solution, particularly as the free base. Thus, it is often desirable to re-purify the de-protected product using purification techniques known in the art. For example, any one or more of the methods described above for separating chiral molecules, such as, chromatography (e.g., HPLC, GC, and SFC), crystallization, fractional crystallization, and the like may be used for re-purification. An exemplary method is recrystallization. Purification by recrystallization allows separation of the desired (S)-enantiomer in high purity, such that the overall reaction sequence including isolation of the desired (S)-enantiomer requires only a single chromatographic step (i.e., the chiral separation). Recrystallization can be carried out in any of a number of single or mixed solvent systems including alcohols, ethers, esters, nitriles, halogenated hydrocarbons, amides and aqueous mixtures thereof. Suitable solvents include methanol, ethanol, propanol, iso-propanol, acetone, tetrahyrofuran, methyl ethyl ketone, methyl isobutyl ketone, ethyl acetate, amyl acetate, acetonitrile, diethyl ether, methyl tert-butyl ether, dichloromethane, dichloroethane, chloroform, dimethylformamide, and combinations thereof. Illustrative mixed solvent systems used to recrystallize (S)-AV1013 are iso-propanol/methyl tert-butyl ether and ethanol/methyl tert-butyl ether.

The resultant (S)-AV1013 hydrochloride appears to form an alcohol solvate when recrystallization is carried out using iso-propanol or ethanol/methyl tert-butyl ether as solvents. The crystals of (S)-AV1013 obtained from recrystallization can be dried at temperatures greater than 50° C. to remove solvent. Alternatively, solvent can be removed from the (S)-AV1013 crystals by drying the crystals under vacuum under controlled humidity conditions (i.e., to displace solvent with water), or by formation of alternative acid salt forms such as the hydrobromide or methanesulfonic acid salts, or the like.

An alternative approach to synthesize the desired (S)-enantiomer of AV1013 includes the formation of an oximinoketone using isopropylpyrazolo[1,5-a]pyridin-3-yl)propan-1-one as the starting material. FIG. 7 and working Example 8 illustrate this synthetic methodology. Accordingly, in one approach using isopropylpyrazolo[1,5-a]pyridin-3-yl)propan-1-one as the starting material (Approach I), the 3-propane-1-one group is further functionalized to introduce an oxime group by nitrosation at the C-α(2-position adjacent to the keto group), to form the corresponding alpha-oximinoketone (Compound C, FIG. 7). Catalytic hydrogenation of the oxime group results in the corresponding amine salt. Optionally enantioselective hydrogenation, may be carried out using chiral catalyst. Any of a number of suitable enantioselective hydrogenation catalysts may be used, such as for example, a platinum catalyst modified with a cinchona alkaloid or a related modifier, or other similar enantioselective hydrogenation catalysts as described in *Handbook of Reagents for Organic Synthesis: Chiral reagents for asymmetric synthesis*, L. Paquette, Ed., Wiley and Sons, 2003. Other suitable approaches for carrying out the reduction include dithionite reduction or zinc/acetic acid reduction. The product is then isolated (or resolved) to provide the desired (S)-AV1013 enantiomer, preferably in the form of an acid salt such as its hydrochloride salt, as described above.

In Approach II, the keto group of 1-(2-isopropylpyrazolo[1,5-a]pyridin-3-yl)propan-1-one is directly converted to an oxime (D) (see FIG. 7). The oxime is then converted to the corresponding oxime tosylate (E), e.g., by reaction with tosyl chloride, followed by a Neber rearrangement under basic conditions to form the desired amino ketone, AV 1013, preferably in the form of an acid addition salt. The desired (S)-enantiomer is then obtained by chiral resolution as previously described. These synthetic methodologies are further described in Example 8.

Pharmacology—Enantiomer-Predominant Pharmacokinetics

As described above, the subject enantiomer, (S)-2-amino-1-(2-isopropylpyrazolo[1,5-a]pyridin-3-yl)propan-1-one (Compound (S)-AV1013), exhibits surprising enantioselective pharmacokinetics when evaluated in suitable animal models. Upon dosing racemic 2-amino-1-(2-isopropylpyrazolo[1,5-a]pyridin-3-yl)propan-1-one, a strong preference for the (S)-enantiomer is seen in-vivo based on the levels of this enantiomer in plasma. Example 2 describes oral dosing of the racemate in both rat and dog. Plasma concentrations of the two enantiomers differed significantly in rat, as indicated by mean peak plasma levels ($C_{max}$): 1.3 μg/mL (S) versus 0.2 μg/mL (R). The calculated area under the curves (AUC) for the (S)- and (R)-enantiomers were 6.0 μg.h/mL for the (S)-enantiomer, and 0.3 μg.h/mL (R) enantiomer. Based on these results, it can be seen that (S) AV1013 possesses a $C_{max}$ when administered orally in rats that is at least 3-fold greater than that of the corresponding (R) enantiomer, or preferably is a least 4-times greater. From the data in Table 1 (below), it can be seen that the $C_{max}$ for (S) AV1013 when administered orally in rats, is more than 6-fold greater than that of the $C_{max}$ for the corresponding (R)-enantiomer, while the AUC for the (S)-enantiomer is around 17-fold greater than the AUC for the corresponding (R) enantiomer, indicating a significantly higher plasma exposure of the (S) over the (R) enantiomer of AV1013. See FIG. 1.

A similar preference for the (S)-enantiomer was observed in dogs orally dosed with AV1013 racemate, although the pharmacokinetic selectivity was not as notable as that seen in rats. As seen in Table 2, mean peak plasma levels ($C_{max}$) for the (S)- and (R)-enantiomers of AV1013 were 2.6 μg/mL and 1.1 μg/mL respectively. The calculated area under the curves (AUC) for the (S)- and (R)-enantiomers were 24.2 μg.h/mL and 7.6 μg.h/mL respectively. Thus, enantioselective pharmacokinetics was also observed in dogs, specifically beagles, orally dosed with AV1013 racemate, as indicated by a >2-fold preference for the S-enantiomer over the (R)-enantiomer based on $C_{max}$ values, and >3-fold preference for the (S)-enantiomer over the (R)-enantiomer based on calculated values for AUC. See FIG. 2.

Moreover, studies by the present inventors have indicated that (S)-AV1013 shows good bioavailability. For example, more than 70% of the (S)-enantiomer dosed is bioavailable with an in vivo duration of action of several hours, for example, from 2-24 hours or greater. (S)-AV1013 also exhibits good water solubility.

(S)-AV1013 exhibits no detectable racemization in vivo. For example, rats dosed with enantiomerically pure (S)-AV1013 (99% enantiomeric excess) showed no detectable plasma levels of the corresponding (R) enantiomer. These results indicate that the in vivo interconversion of the (S)- to the (R)-enantiomer is not significant. Examination of dosing solutions and solutions used for analysis of the kinetics and extent of racemization reveal no detectable interconversion between the enantiomers.

Methods and Efficacy

Based upon the pharmacokinetic data for (S)-AV-1013 obtained from rats and dogs, it can be seen that enantiopure (S)-AV1013 should exhibit greater potency in vivo than the corresponding (R)-isomer or racemic mixture. Thus, (S)-AV1013 is a suitable candidate therapeutic for treating a variety of disease conditions, including for the treatment of neuropathic pain, inflammatory conditions including inflammatory pain, opioid addiction and withdrawal behaviors.

Figure 3:
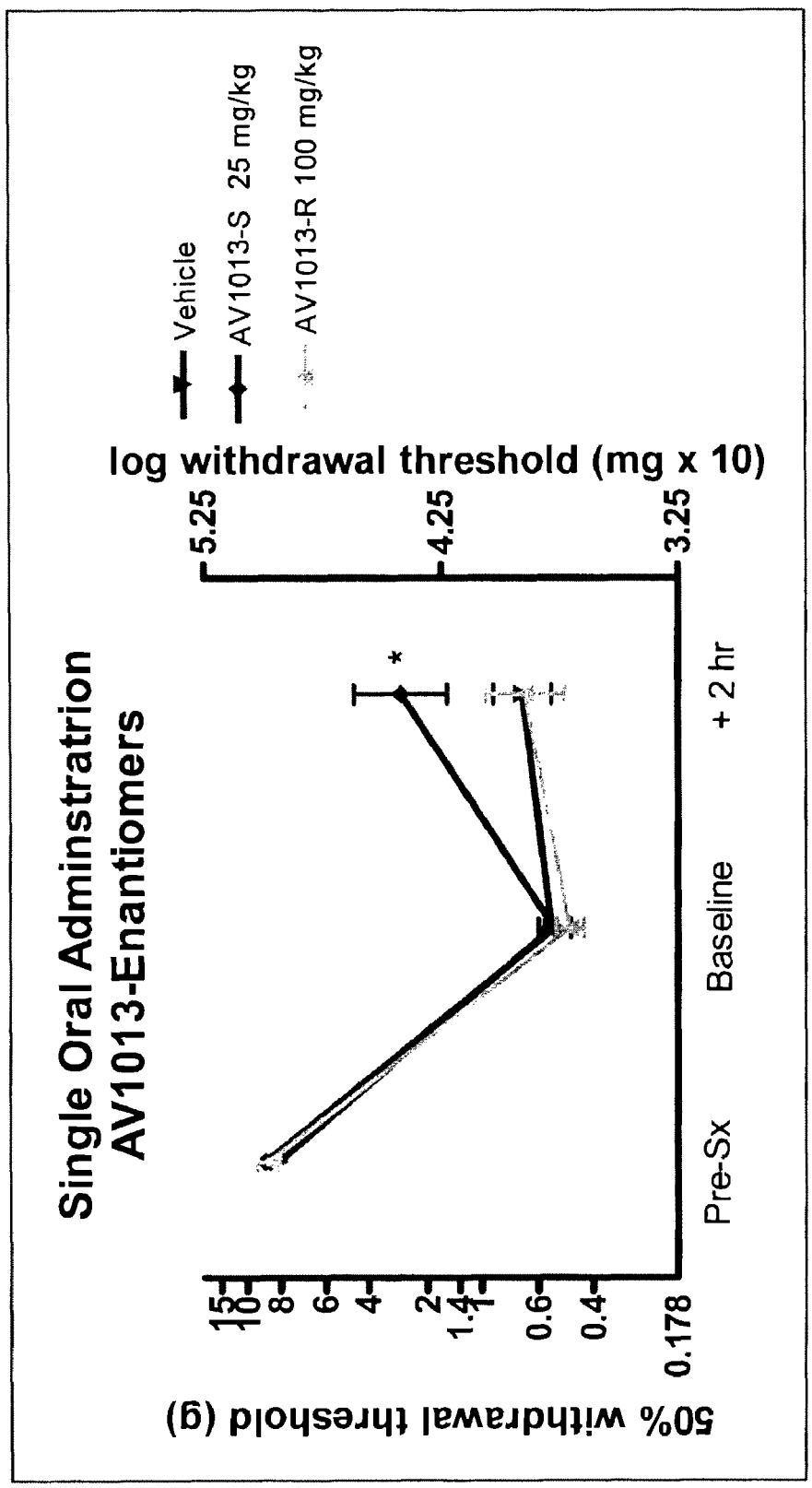
As shown in FIG. 3, plasma concentration levels of the (S)-enantiomer of AV1013 are higher than those of the (R)-enantiomer over 24 hours time interval.

Example 3 and the data illustrated in FIG. 3 show that (S)-AV1013 is substantially more potent in treating neuropathic pain than the corresponding (R) enantiomer when both enantiomers are administered orally at the same dose. Indeed, the (R) enantiomer appears to demonstrate essentially no activity in the neuropathic pain model employed, as indicated by a potency that is essentially the same as that of the vehicle, even at four times the dosage amount of the (S)-enantiomer.

Thus, (S)-AV1013 may be used to treat neuropathic pain associated with certain disease states (syndromes) such as viral neuralgias (e.g., herpes, AIDS), diabetic neuropathy, phantom limb pain, stump/neuroma pain, post-ischemic pain (stroke), fibromyalgia, reflex sympathetic dystrophy (RSD), complex regional pain syndrome (CRPS), cancer pain, vertebral disk rupture, spinal cord injury, and trigeminal neuralgia, cancer-chemotherapy-induced neuropathic pain, spinal cord injury, and migraine, among others. Given the potential for broader anti-inflammatory activity, other inflammatory conditions such as rheumatoid arthritis, osteoarthritis, autoimmune illnesses and even sepsis are likely indicated for clinical intervention with the (S)-enantiomer—and likely at efficacious dosage amounts that are reduced from those of the racemate or the (R)-enantiomer.

Figure 5A:
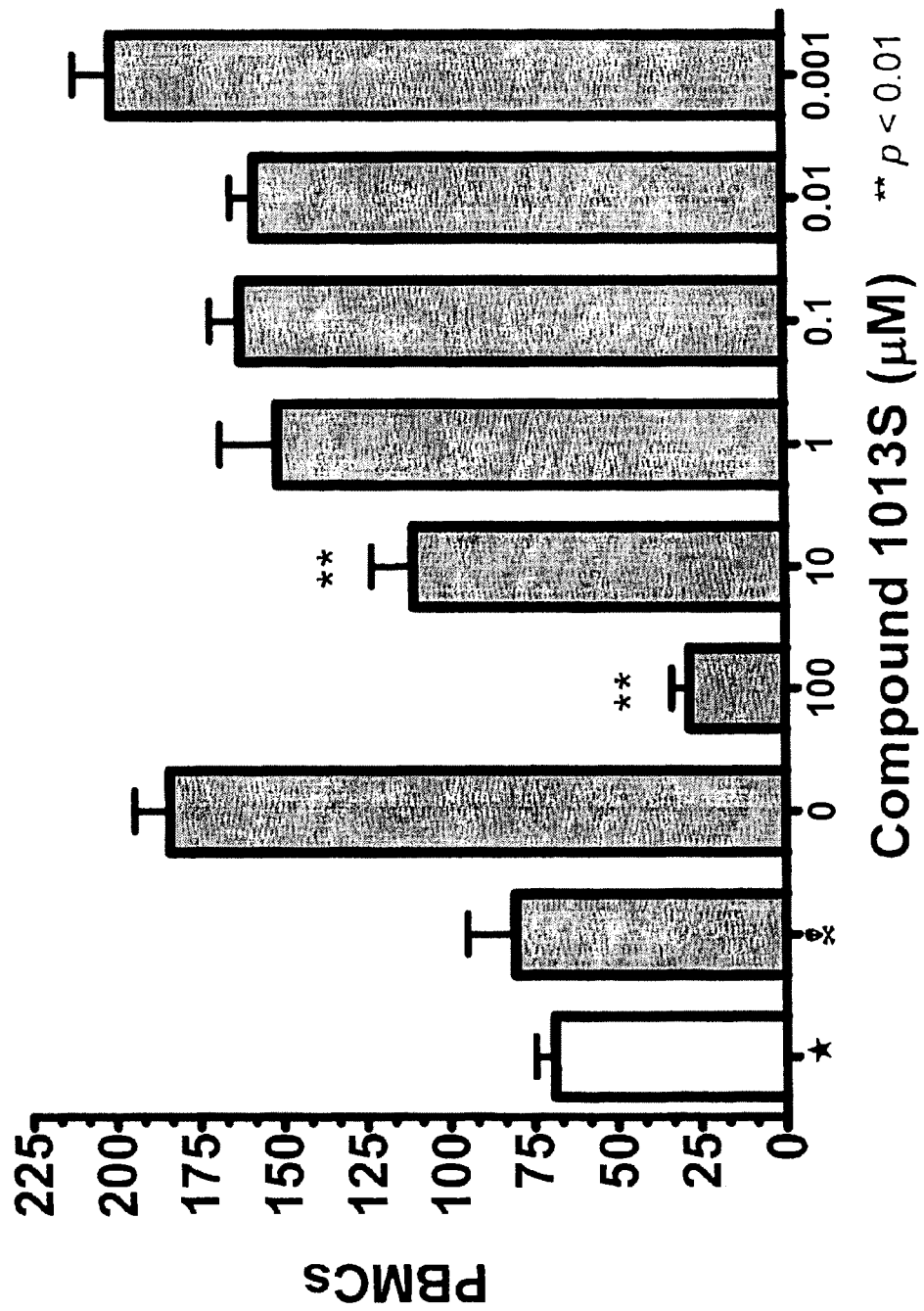
FIGS. 5A and 5B illustrate the effect of varying concentrations of (S)-AV1013 (FIG. 5A) and (R))-AV1013 (FIG. 5B) on inhibition of human peripheral blood monocytes (PBMCs) migration in response to the pro-inflammatory cytokine, MIF, as described in detail in Example 6.
Figure 5B:
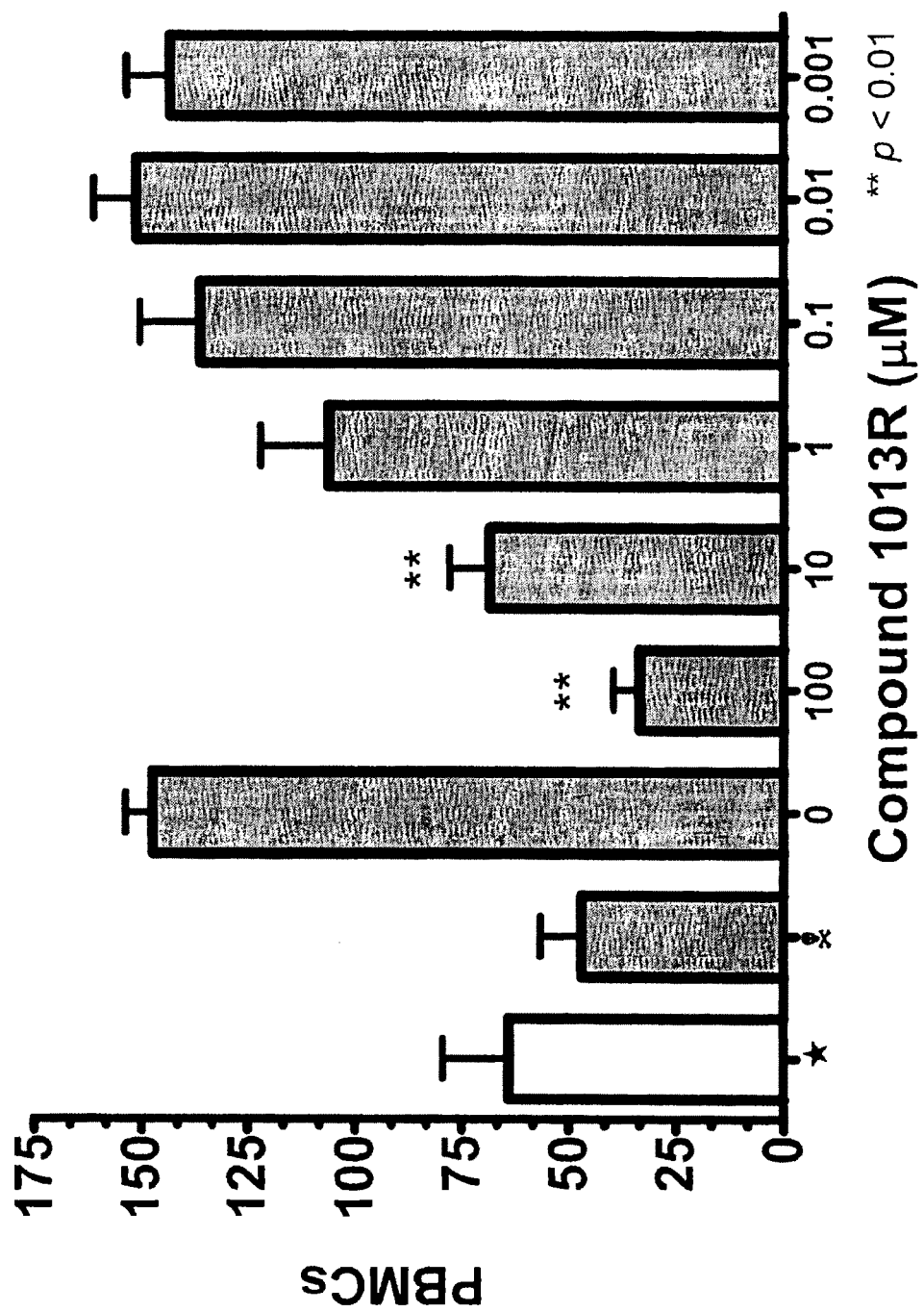

Based upon results from both a standard mouse model of inflammatory pain as described in Example 4 and a macrophage migration inhibitory (MIF) assay as described in Example 6, the inventive compound (S)-2-amino-1-(2-isopropylpyrazolo[1,5-a]pyridin-3-yl)propan-1-one exhibits analgesic/anti-inflammatory activity. As demonstrated in Example 4, (S)-AV1013 was quite effective when evaluated in a formalin paw model and administered in a single 50 mg/kg dose in mice. As can be seen from the results in Table 3, administration of (S)-AV1013 notably reduced the number of occasions that mice lick their paw following interplantar injection of formalin (−45%) in comparison to control. Moreover, when examined in a MIF assay, both (S)-AV1013 and (R)-AV1013 were discovered to antagonize MIF-induced mononuclear cell migration in a similar dose dependent fashion as illustrated in FIGS. 5A and 5B. MIF is a pro-inflammatory cytokine that functions to regulate macrophage function and is implicated in multiple inflammatory disease conditions. Thus, the ability of both enantiomers of AV1013 to antagonize macrophage migration provides an indication, in addition to the other supporting data provided herein, of its anti-inflammatory activity. However, the surprising finding that (R)-AV1013 has very low circulating plasma levels upon oral dosing relative to the (S) enantiomer, makes the (R) enantiomer much less suitable as a potential therapeutic. In light of the foregoing, enantiopure (S)-1013 can be used to treat any of a number of inflammatory conditions. Representative inflammatory disorders that may be treated by administering a compound as described herein include rheumatoid arthritis, bronchitis, tuberculosis, chronic cholecystitis, inflammatory bowel disease, osteoarthritis, acute pancreatitis, sepsis, asthma, chronic obstructive pulmonary disease, dermal inflammatory disorders such as psoriasis and atopic dermatitis, systemic inflammatory response syndrome (SIRS), acute respiratory distress syndrome (ARDS), cancer-associated inflammation, reduction of tumor-associated angiogenesis, osteoarthritis, diabetes, treatment of graft v. host disease and associated tissue rejection, Crohn's disease, delayed-type hypersensitivity, immune-mediated and inflammatory elements of CNS disease; e.g., Alzheimer's, Parkinson's, multiple sclerosis, etc.

Figure 4:
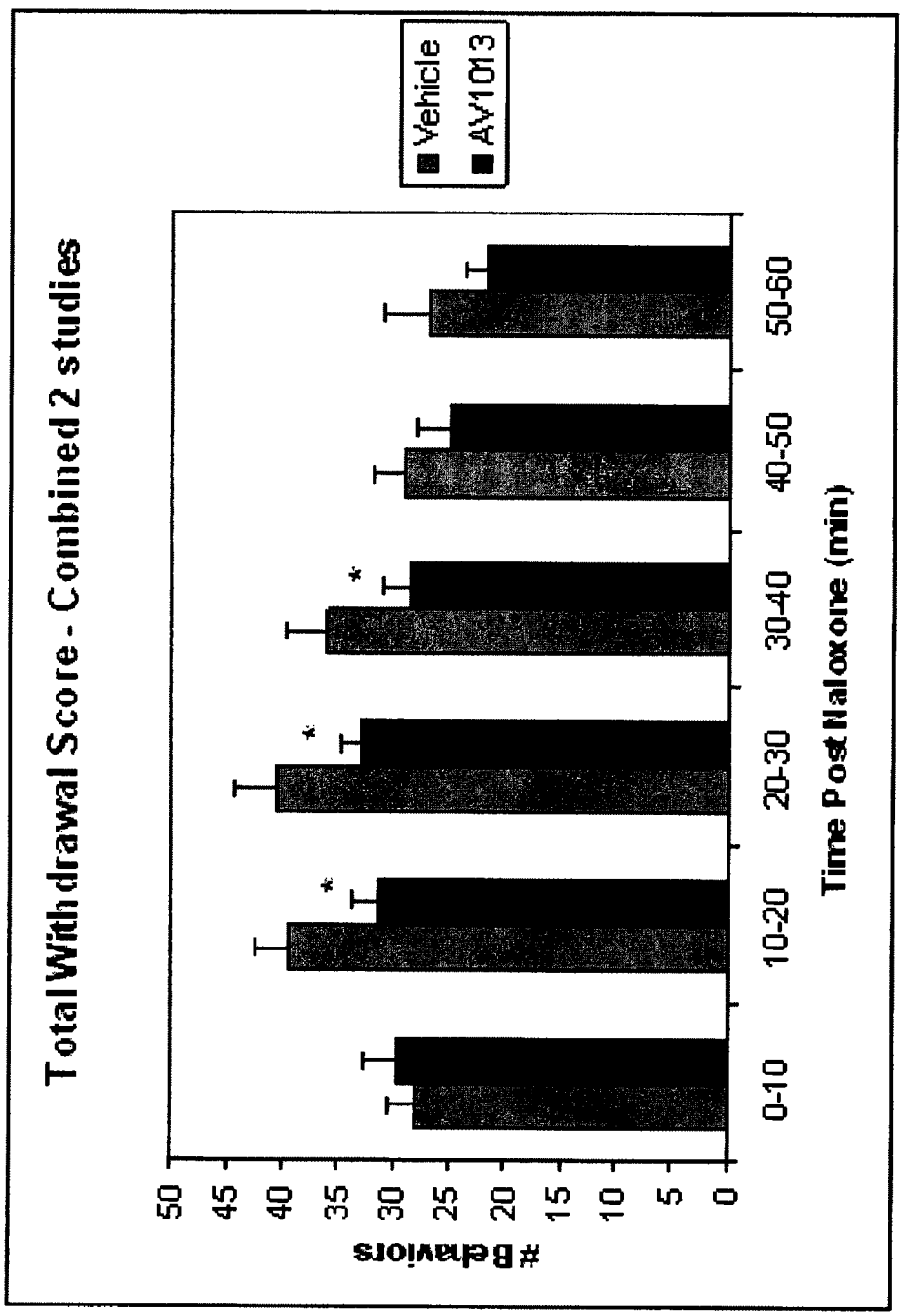
FIG. 4. illustrates the ability of (S)-AV1013 to attenuate classic withdrawal behaviors in rats relative to the control in a rat opioid withdrawal model as described in detail in Example 5.

The subject enantiomer is also effective in reducing/ameliorating the symptoms of morphine withdrawal behavior as indicated in Example 5 and illustrated graphically in FIG. 4. When evaluated in a rat morphine withdrawal model, rats administered (S)-AV1013 demonstrated reduced withdrawal symptoms relative to those receiving vehicle. For example, the (S)-enantiomer may be administered to a subject to treat a drug addiction. The subject may be addicted to one or more drugs including, but not limited to, psychostimulants, narcotic analgesics, alcohols and addictive alkaloids, such as nicotine, cannabinoids, or combinations thereof. Exemplary psychostimulants include, but are not limited to, amphetamine, dextroamphetamine, methamphetamine, phenmetrazine, diethylpropion, methylphenidate, cocaine, phencyclidine, methylenedioxymethamphetamine and pharmaceutically acceptable salts thereof. Exemplary narcotic analgesics include, but are not limited to, alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine and pharmaceutically acceptable salts thereof. Addictive drugs also include central nervous system depressants, including, but not limited to, barbiturates, chlordiazepoxide, and alcohols, such as ethanol, methanol, and isopropyl alcohol.

The subject enantiomer, (S)-2-amino-1-(2-isopropylpyrazolo[1,5-a]pyridin-3-yl)propan-1-one (Compound (S)-AV1013), may also be used to treat a behavior addiction. Behavioral addiction can include, but is not limited to, compulsive eating, drinking, smoking, shopping, gambling, sex, and computer use. Addiction-related behavior in reference to a drug addiction includes behavior resulting from compulsive use of a drug characterized by dependency on the substance. Symptomatic of the behavior is (i) overwhelming involvement with the use of the drug, (ii) the securing of its supply, and (iii) a high probability of relapse after withdrawal.

Decreased binding of (S)-AV1013 at the Rolipram binding site at a therapeutically meaningful concentration of 10 uM was observed with the enantiomerically pure S-enantiomer. Because inhibition at the Rolipram binding site is implicated to result in undesired side effects, such as nausea and emesis (Duplantier et al. *J Med Chem* 1996 Jan. 5; 39(1):120-5), it is desirable for the therapeutic agent to exhibit a decreased binding inhibition at this site. Studies conducted by these inventors in rodents and dogs have shown that while racemic AV1013 at a concentration of 10 uM results in 43% inhibition of the Rolipram binding site, the enantiomerically pure (S) enantiomer exhibits only 12% inhibition. These results provide further support for the use of (S)-AV1013 as a candidate therapeutic in treating withdrawal symptoms and behavioral addiction problems in mammals, especially humans.

Administration (S)-AV1013) may be administered either systemically or locally. Such routes of administration include but are not limited to, oral, intra-arterial, intrathecal, intraspinal, intramuscular, intraperitoneal, intravenous, intranasal, subcutaneous, and inhalation routes.

More particularly, (S)-AV1013 may be administered for therapeutic use by any suitable route, including without limitation, oral, rectal, nasal, topical (including transdermal, aerosol, buccal and sublingual), vaginal, parenteral (including subcutaneous, intramuscular, intravenous and intradermal), intrathecal, anal (suppository) and pulmonary. The preferred route will, of course, vary with the condition and age of the recipient, the particular condition being treated, and the specific combination of drugs employed, if any.

One preferred mode of administration (depending upon the particular condition being treated) is directly to neural tissue such as peripheral nerves, the retina, dorsal root ganglia, neuromuscular junction, as well as the CNS, e.g., to target spinal cord glial cells by injection into, e.g., the ventricular region, as well as to the striatum (e.g., the caudate nucleus or putamen of the striatum), spinal cord and neuromuscular junction, with a needle, catheter or related device, using neurosurgical techniques known in the art, such as by stereotactic injection (see, e.g., Stein et al., *J. Virol.* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000). A particularly preferred method for targeting spinal cord glia is by intrathecal delivery, rather than into the cord tissue itself.

Another preferred method for administration is by delivery to dorsal root ganglia (DRG) neurons, e.g., by injection into the epidural space with subsequent diffusion to DRG. For example, the (S)-enantiomer can be delivered via intrathecal cannulation under conditions effective to diffuse the composition to the DRG. See, e.g., Chiang et al., *Acta Anaesthesiol. Sin.* (2000) 38:31-36; Jain, K. K., *Expert Opin. Investig. Drugs* (2000) 9:2403-2410.

Yet another mode of administration to the CNS uses a intra-brain convection-enhanced delivery (CED) system. In this way, (S)-AV1013 can be delivered to many cells over large areas of the CNS. Any convection-enhanced delivery device may be appropriate for delivery of the subject (S)-enantiomer.

The compositions described herein encompass all types of formulations and, in particular, those that are suited for systemic or intrathecal administration.

Dose

Therapeutic amounts can be empirically determined and will vary with the particular condition being treated, the subject, and the efficacy and toxicity of the (S)-enantiomer. The actual dose to be administered will vary depending upon the age, weight, and general condition of the subject as well as the severity of the condition being treated and the judgment of the health care professional.

Therapeutically effective amounts can be determined by those skilled in the art, and will be adjusted to the requirements of each particular case—i.e., subject, condition, treatment regime, mode of delivery, etc. Generally, a therapeutically effective amount of the (S)-enantiomer will range from a total daily dosage of about 0.1 and 1000 mg/day, more preferably, in an amount between 1-200 mg/day, 30-200 mg/day, 1-100 mg/day, 30-100 mg/day, 30-300 mg/day, 1-60 mg/day, 1-40 mg/day, 10-30 mg/kg or 1-10 mg/day, administered as either a single dosage or as multiple dosages.

Preferred dosage amounts include dosages greater than or equal to about 10 mg BID, or greater than or equal to about 10 mg TID, or greater than or equal to about 10 mg QID. That is to say, a preferred dosage amount is greater than about 10 mg/day or greater than 30 mg/day. Dosage amounts may be selected from 30 mg/day, 50 mg/day, 70 mg/day, 90 mg/day or 150 mg/day, 500 mg/day or more. Depending upon the dosage amount and precise condition to be treated, administration can be one, two, or three times daily for a time course of one day to several days, weeks, months, and even years, and may even be for the life of the patient. Alternatively, administration can be every other day, three times weekly, twice weekly, once weekly, twice monthly, once monthly, and so forth. Illustrative dosing regimes will last a period of at least about a week, from about 1-4 weeks, from 1-3 months, from 1-6 months, from 1-50 weeks, from 1-12 months, or longer.

Formulations

In one embodiment, the present invention provides formulations of (S)-AV1013 that are suitable for oral and intrathecal use. For example, oral dosage forms include tablets, lozenges, capsules, syrups, oral suspensions, emulsions, granules, and pellets. In another embodiment, formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

Formulations suitable for parenteral administration include aqueous and non-aqueous isotonic sterile solutions suitable for injection, as well as aqueous and non-aqueous sterile suspensions. Parenteral formulations are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation may also be a sustained release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the invention may optionally include other agents conventional in the pharmaceutical arts and specific to type of formulation being employed. That is, formulations of (S)-AV1013, may optionally contain one or more additional components or excipients as described below.

For example, a therapeutic composition may comprise, in addition to (S)-AV1013, one or more pharmaceutically acceptable excipients or carriers. Exemplary excipients include, without limitation, polyethylene glycol (PEG), hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like. Representative vehicles include water and saline. Additionally, (S)-AV1013 formulations suitable for oral administration may also include additional agents as sweeteners, thickeners or flavoring agents.

The amount of any individual excipient in the composition will vary depending on the role of the excipient, the dosage requirements of the active agent components, and particular needs of the composition. Typically, the optimal amount of any individual excipient is determined through experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in an composition comprising a substituted pyrazolo[1,5-a]pyridine is selected from at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", 19th ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

A formulation (or kit) may contain, in addition to the subject enantiomer, one or more additional active agents, e.g., a drug effective for treating neuropathic pain. Such actives include gabapentin, memantine, pregabalin, morphine and related opiates, cannabinoids, tramadol, lamotrigine, carbamazepine, duloxetine, milnacipran, and tricyclic antidepressants.

Preferably, the composition is formulated in order to improve stability and extend the half-life of the active agent. For example, the (S)-enantiomer may be delivered in a sustained-release formulation. Controlled or sustained-release formulations are prepared by incorporating (S)-enantiomer into a carrier or vehicle such as liposomes, non-resorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, a substituted pyrazolo[1,5-a]pyridine of the invention can be encapsulated, adsorbed to, or associated with, particulate carriers. Examples of particulate carriers include those derived from poly(methyl methacrylate)polymers, as well as microparticles derived from poly(lactides) and poly(lactide-co-glycolides), known as PLG. See, e.g., Jeffery et al., Pharm. Res. (1993) 10:362-368; and McGee et al., J. Microencap. (1997).

The compositions of the present invention may also be prepared in a form suitable for veterinary applications.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

EXAMPLES

It is to be understood that while the invention has been described in conjunction with certain preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains or as otherwise noted in specification.

Example 1

Synthesis of (S)-2-amino-1-(2-isopropylpyrazolo[1,5-a]pyridin-3-yl)propan-1-one hydrochloride (S)-2-Amino-1-(2-isopropylpyrazolo[1,5-a]pyridin-3-yl) propan-1-one hydrochloride (also referred to herein as S-AV1013.HCl) was prepared on a preparative scale using two different routes to obtain the intermediate isopropylpyrazolo[1,5-a]pyridine (IPPP). In the first approach (method 1), ibudilast was employed as the starting material to obtain IPPP; an alternate synthetic approach (method 2) employed ibudilast acid as the starting material.

Step 1

Method 1

Preparation of Isopropylpyrazolo[1,5-a]pyridine (IPPP) from ibudilast

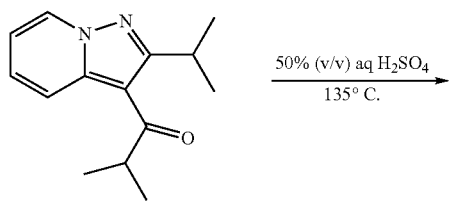

Chemical Formula: $C_{14}H_{18}N_2O$
Molecular Weight: 230.31
C, 73.01; H, 7.88; N, 12.16; O, 6.95
Ibudilast

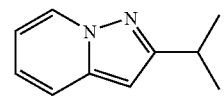

Chemical Formula: $C_{10}H_{12}N_2$
Molecular Weight: 160.22
C, 74.97; H, 7.55; N, 17.48
IPPP
A A 5 L 3-neck round-bottom flask was equipped with a mechanical stirrer, thermocouple, heating mantle and a Y-adapter with a nitrogen inlet. The flask was charged with water (350 mL, USP), concentrated sulfuric acid (350 mL) and ibudilast (3-isobutyryl-2-isopropylpyrazolo[1,5-a]pyridine) (140 g, 0.608 mol). The flask was purged with nitrogen, and the mixture was stirred while it was heated to 135° C. An aliquot was removed for HPLC analysis, which showed that all starting material was consumed after 5 hours at 135° C., so the mixture was allowed to cool to room temperature overnight. The mixture was cooled in an ice bath, and water (1400 mL, USP) was added over 10 min, with the temperature maintained below 25° C. With continuous cooling in an ice bath, the mixture was neutralized by adding sodium hydroxide (50% w/w aq., 1150 mL) dropwise, with the temperature maintained below 25° C. Ethyl acetate (250 mL) was added, and the layers were separated. The aqueous layer was washed with ethyl acetate (2×300 mL). The combined ethyl acetate extracts were washed sequentially with 250 mL portions of saturated aqueous sodium bicarbonate and saturated aqueous sodium chloride, then dried over anhydrous sodium sulfate for 30 minutes. Activated carbon (20 g) and silica (60 g) were added and stirred before filtering over a pad of Celite. The filtrate was concentrated under reduced pressure to obtain 96.5 g of IPPP (2-isopropyl-pyrazolo[1,5-a]pyridine, 99% crude yield, 99.6 area % pure by HPLC) as an amber oil.

$^1$H-NMR (CDCl$_3$) δ 1.4 (d, 6H), 3.2 (m, 1H), 6.3 (s, 1H), 6.6 (t, 1H), 7.0 (m, 1H), 7.4 (d, 1H), 8.4 (d, 1H). HPLC: RT=9.1 min (99.6 area %).

Step 1

Method 2

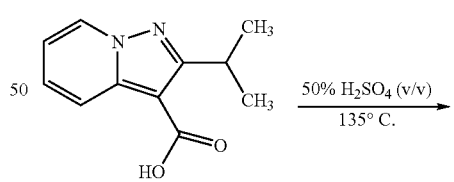

Ibudilast Acid
$C_{11}H_{12}N_2O_2$
204.23 g/mol

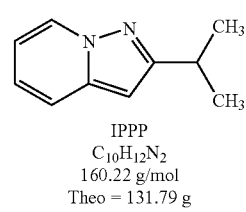

IPPP
$C_{10}H_{12}N_2$
160.22 g/mol
Theo = 131.79 g

A 5 L 3-neck round-bottom flask was equipped with a mechanical stirrer, thermocouple, heating mantle and a Y-adapter with a nitrogen inlet. The flask was charged with water (420 mL, USP), conc. sulfuric acid (420 mL) and ibudilast acid (2-isopropyl-pyrazolo[1,5-a]pyridin-3-carboxylic acid, 168 g, 0.823 mol). The flask was purged with nitrogen, and the mixture was stirred and slowly heated to 135° C. over 1.5 h. An aliquot was removed for HPLC analysis, which showed that all starting material was consumed, so the mixture was allowed to cool to room temperature overnight. The mixture was cooled in an ice bath, and water (1680 mL, USP) was added over 10 min, with the temperature maintained below 35° C. With continuous cooling in an ice bath, the mixture was neutralized by adding sodium hydroxide (50% w/w aq., 1420 mL) dropwise over about 40 min, with the temperature maintained below 35° C. Dichloromethane (300 mL) was added, the cooling bath was removed, and the mixture was stirred for 30 min. The layers were separated, and the aqueous layer was washed with dichloromethane (2×300 mL). Additional water was added as needed to keep the inorganic solids from precipitating during the extraction. The combined dichloromethane extracts were washed sequentially with 400 mL portions of water (USP) and saturated aqueous sodium chloride, then dried over anhydrous sodium sulfate. The dichloromethane solution was filtered and concentrated under reduced pressure to obtain 126 g of IPPP (2-isopropyl-pyrazolo[1,5-a]pyridine, 96% crude yield, 99 area % pure by HPLC) as an amber oil. HPLC: RT=9.1 min (99 area %).

Step 2

2-Chloro-desmethylibudilast from IPPP

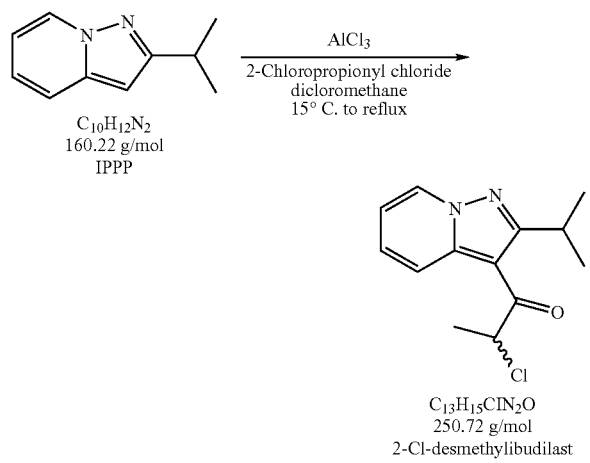

A 5 L three-neck round bottom flask, equipped with a mechanical stirrer, thermocouple, reflux condenser and nitrogen inlet, was flushed with nitrogen and charged with dichloromethane (825 mL). Aluminum chloride (418 g, anhydrous) was charged to the reactor, with the aid of a dichloromethane rinse (150 mL). The mixture was stirred and cooled to 15° C. with an ice-water bath, and IPPP (2-isopropyl-pyrazolo[1,5-a]pyridine, 125 g, 0.78 mol) was added dropwise via an addition funnel over about a 15 minute period, with the temperature maintained at 15-20° C. Dichloromethane (100 mL) was used to rinse the residual IPPP from the funnel into the reactor. The mixture was stirred for 10 min at this temperature, then 2-chloropropionyl chloride (155 mL, 1.56 mol) was added dropwise via addition funnel over about a 10 minute period, with the temperature maintained at 15-20° C. Dichloromethane (100 mL) was used to rinse the residual 2-chloropropionyl chloride into the reactor. The cooling bath was removed and stirring was continued for 15 min, then the mixture was heated to reflux.

After 20 h at reflux, the mixture was cooled to <20° C. and added slowly over about a 1 h period with stirring, to ice-water (1250 mL) cooled in an ice-water bath with the temperature maintained below 35° C. The resulting mixture was stirred at 15-20° C. for 10 min, then the dark brown organic layer was collected. The aqueous layer was washed with dichloromethane (2×125 mL). The combined organic extracts were stirred with 1 M NaOH (800 mL) for 30 min. The organic layer was separated and the aqueous layer was washed with dichloromethane (2×100 mL). The combined organic extracts were washed successively with water (500 mL, USP), saturated aqueous NaCl (650 mL) and then dried with stirring over anhydrous sodium sulfate. Silica gel (98 g) and activated carbon (DARCO, 29 g) were added and stirring was continued for 30 min. The dichloromethane was filtered through Celite and the drying agent and celite were rinsed with dichloromethane (3×400 mL). The mixture was concentrated by distillation at ambient pressure. When about 1.5 L of distillate was removed, heptane (1.6 L) was added and distillation was continued until the pot temperature reached 83° C. The mixture was allowed to cool slowly with stirring. After seeding and cooling to <10° C. for 1 h, the resulting precipitate were collected by filtration, rinsed with heptane (400 mL) and dried to obtain 165 g of chloroketone (84% yield) as an off-white solid.

$^1$H-NMR (DMSO-d6) δ 1.3 (m, 6H), 1.7 (d, 3H), 3.7 (m, 1H), 5.4 (q, 1H), 7.2 (t, 1H), 7.7 (t, 1H), 8.1 (d, 1H), 8.9 (d, 1H). HPLC: RT=11.5 min (100 area %).

Step 3

Racemic AV1013 trifluoroacetamide from 2-Chloro-nor-methylibudilast

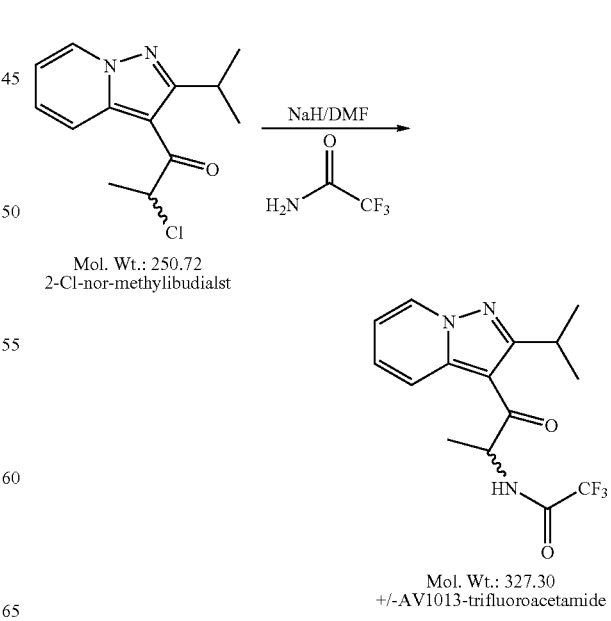

A 3 L three-neck round bottom flask, equipped with a mechanical stirrer, thermocouple, reflux condenser and nitrogen inlet, was flushed with nitrogen and charged with sodium hydride (37.3 g, 60% in mineral oil, 0.933 mol) and dimethylformamide (780 mL). The mixture was stirred and cooled to <5° C. in an ice-water bath. Trifluoroacetamide was added in portions with the temperature maintained at <20° C. The resulting beige slurry was stirred for 0.5 h at <5° C., then the chloroketone was added. The cooling bath was removed and the mixture was allowed to warm to ambient temperature with stirring. After 26 h, the mixture was cooled in an ice-water bath and the temperature was maintained at <10° C. while water (1.56 L) was added over about a 40 min period. After stirring and cooling for another 2 h, the resulting solids were collected by filtration and rinsed with water (1.39 L) and dried at 50° C. under vacuum. The resulting beige solid was slurried in heptane (540 mL) at 50° C. for 1 h, then the mixture was cooled slowly to <5° C. After cooling for 1.5 h, the solids were collected by filtration, washed with heptane (540 mL) and dried at 50° C. under vacuum to obtain 88 g (87% yield) of the trifluoroacetamide as a beige solid.

$^1$H-NMR (CDCl$_3$) δ 1.4 (m, 6H), 1.6 (d, 3H), 3.7 (m, 1H), 5.3 (m, 1H), 7.0 (t, 1H), 7.5 (t, 1H), 7.9 (bs, 1H), 8.0 (d, 1H), 8.5 (d, 1H). Elem. anal. calcd. for C$_{15}$H$_{16}$F$_3$N$_3$O$_2$, C, 55.04; H, 4.93; F, 17.41; N, 12.84. found C, 54.92; H, 4.88, F, 17.65; N, 12.76. HPLC: RT=10.5 min.

Step 4

Preparation of (R)-AV103 trifluoroacetamide and (S)-AV103 trifluoroacetamide

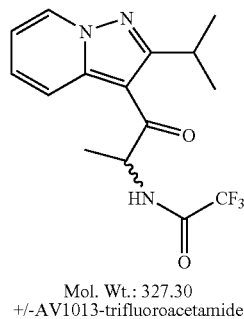

Mol. Wt.: 327.30
+/-AV1013-trifluoroacetamide

SFC Chromatography
Whelk-O-01 Column

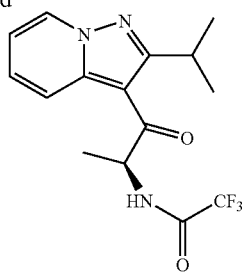

Mol. Wt.: 327.30
(S)-AV1013-trifluoroacetamide

Chiral separation of AV1013 trifluoroacetamide was carried out under the following conditions using supercritical fluid chromatography.

Column: Whelk-O-01, 50 mm×250 mm

Isocratic mobile phase; CO$_2$.Ethanol (90:10)

Flow rate: 250 g/min

UV Detector: 254 nm

Loading Solution: (+/−)-AV1013-trifluoroacetamide 75 mg/mL in methanol

Injection Volume: 3 mL

Injection Cycle Time: 2.5 minutes (+/−)-AV1013-trifluoroacetamide: 88 g

| Analysis (Chiral HPLC) | | | |
|---|---|---|---|
|  |  | % (R) | % (S) |
| Fraction 1: | 37.1 g | 99.9 | 0.1 |
| Fraction 2: | 10.2 g | 1.8 | 98.2 |
| Fraction 3: | 23.1 g | 1.1 | 98.9 |

Column: (S,S) Whelk-O, 250×4.6 mm, 30° C.

Eluant: isocratic, 80:20 hexane:isopropanol, 1.5 mL/min

UV Detector: 254 nm (R)-AV1013-trifluoroacetamide, RT=3.2 min (S)-AV1013-trifluoroacetamide, RT=4.2 min Step 5

Preparation of (S)-AV1013.HCl

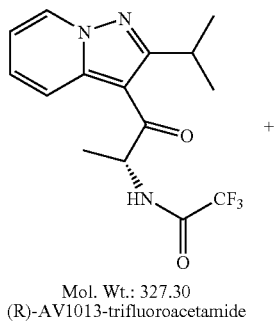

Mol. Wt.: 327.30
(R)-AV1013-trifluoroacetamide

+

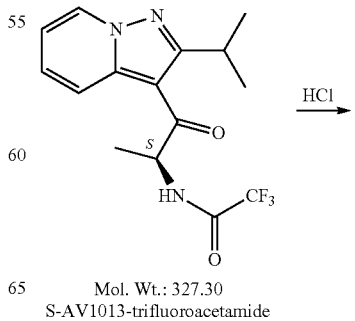

Mol. Wt.: 327.30
S-AV1013-trifluoroacetamide

HCl →

-continued

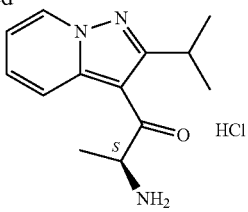

Mol. Wt.: 267.75
S-AV1013-HCl

A 500 mL round bottom flask was fitted with a magnetic stirrer and thermostatted heating unit and charged with (S)-AV1013-trifluoroacetamide (20.8 g, 63.6 mmol) and 6 N HCl (208 mL). The resulting beige slurry was heated to 50° C. After heating for 46 h, the mixture was concentrated under reduced pressure at 45° C. Three times, the residue was diluted with absolute ethanol (100 mL) and concentrated under reduced pressure to obtain a yellow solid (18 g). The solid was suspended in abs. ethanol (51 mL) and heated to 55° C. The resulting orange solution was diluted with MTBE (tert-butyl methyl ether, 103 mL) and cooled slowly to 5° C. The resulting solid precipitate was collected by filtration, rinsed with MTBE (34 mL) and dried. This solid was heated to 55° C. in abs. ethanol (37 mL) and the mixture was diluted with MTBE (75 mL) and cooled slowly to 5° C. The resulting solid was collected by filtration, rinsed with MTBE (24 mL) and dried at 50° C. under vacuum to obtain 10.0 g (56% yield) of (S)-AV1013.HCl.0.3 EtOH (F.W. 281.58) as a white solid. 97.2% S/2.8% R by chiral HPLC.

$^1$H-NMR (DMSO-d6) δ 1.31 (d, 3H), 1.36 (d, 3H), 1.45 (d, 3H), 3.70 (m, 1H), 4.77 (q, 1H), 7.22 (t, 1H), 7.72 (t, 1H), 8.07 (d, 1H), 8.4 (bs, 3H), 8.92 (d, 1H). FT-IR (KBr) 2874, 1652, 1632, 1505, 967, 757 cm$^{-1}$. Elem. anal. calcd. for $C_{13.6}H_{19.8}ClN_3O_{1.3}$[(S)-AV1013.HCl.0.3 EtOH]C, 58.01; H, 7.09; Cl, 12.59; N, 14.92. found C, 57.83; H, 7.20; Cl, 12.71; N, 14.82.

Analytical Chiral HPLC Method:
Column: (S,S) Whelk-O, 250×4.6 mm, 30° C.
UV Detector: 220 nm
Eluent: isocratic, 92:8:0.5 hexane:ethanol:diethylamine, 2 mL/min
(R)-AV1013, RT=9.6 min (S)-AV1013, RT=11.2 min
Analytical Reverse-Phase HPLC Method:
Column: Waters Nova-Pak C18, 4 urn, 150×3.9 mm, 40° C.;
UV Detector: 292 nm
Eluent A: 95:5 10 mM K3PO4 acidified to pH 3 with 85% phosphoric acid:acetonitrile
Eluent B: 5:95 10 mM K3PO4 acidified to pH 3 with 85% phosphoric acid:acetonitrile:

| Gradient: | | |
| --- | --- | --- |
| Time (min.) | % B | Flow Rate |
| 0.0 | 10 | 1.5 mL/min |
| 20.0 | 80 | " |
| 25.0 | 80 | " |
| 25.1 | 10 | " |
| 30.0 | 10 | " |

AV1013, RT=2.4 min
The five-step route provided a 15% overall yield of (S)-AV1013.HCl. The chiral separation, by SFC chromatography, is the only chromatographic step required. Hydrolysis of the N-protected (S)-AV1013, followed by recrystallization from iso-propanol/methyl tert-butyl ether provided (S)-AV1013.HCl in greater than 99% chemical purity and greater than 97% S-enantiomer (greater than 94% enantiomeric excess (ee)) by chiral HPLC, as determined from the equation ee=[|R−S$^{51}$÷(R+S)]×100 ee=[|R−S|÷(R+S)]×100. The (S)-enantiomer, even in acid salt form (e.g., as the hydrochloride salt), proved to be somewhat susceptible to racemization following cleavage of the trifluoroacetamide protecting group and subsequent storage. Even under optimal storage and handling conditions to minimize exposure to moisture, a small degree of racemization (i.e., approximately 2%) was observed. Recrystallization was effective to improve enantiomeric purity to arrive at a product having an illustrative chiral purity as described above. Recrystallization proved effective to remove up to about 2% of the (R)-enantiomer, resulting in (S)-AV1013 with ee≧96%. The recrystallized (S)-AV 1013.HCl contained approximately 25 mole percent alcohol (less than about 10% by weight) even when dried at 50° C. Thus, it appears that the resultant product is formed as a solvate under the recrystallization and drying conditions employed.

Example 2

Pharmacokinetics of Racemic AV1013

Racemic AV1013 was dosed in both rats and dogs to examine the pharmacokinetics of the two enantiomers.
Rat Pharmacokinetics:
Three male Sprague-Dawley rats were dosed orally via gavage with 25 mg/kg racemic AV1013 dissolved in water. Serial blood samples were collected from the tail vein at 5, 15, and 30 min, 1, 3, and 6 hours post dosing. Samples were processed for plasma via centrifugation and plasma samples were stored frozen prior to analysis.
Dog Pharmacokinetics:
Three male beagle dogs were dosed orally with 10 mg/kg racemic AV1013 via gavage. AV1013 was dissolved in water at 5 mg/ml and dosed via gavage at a volume of 2 ml/kg. Blood samples were collected via the jugular vein at 5, 15 and 30 minutes, 1, 2, 4, 6, 8, and 24 hours post dosing.
Bioanalytical Method:
A sensitive and specific chiral HPLC/MS/MS bioanalytical method for the detection of (S)-AV1013 and (R)-AV1013 enantiomers in rat and dog plasma was utilized. AV1013 enantiomers and the internal standard (AV1040, an analog of AV1013) were isolated from plasma by protein precipitation induced by acetonitrile. After centrifugation to sediment the proteins, the supernatant fractions were analyzed by high performance liquid chromatography (LC) in conjunction with a triple quadrupole mass spectrometer that used electrospray ionization in tandem with positive ionization (MS/MS) according to the conditions below. The LLOQ (lower level of quantitation) was typically <3 ng/mL.
Mobile Phase: A-25 mM ammonium acetate water; B-acetonitrile
Column: 100×4 mm ChromTech AGP-Chiral HPLC column
Injection Volume: 20 µL
Isocratic Conditions: 7% B for 8 minutes
Flow Rate: 800 µL/min
Mass Spectrometer: Applied Biosystems/MDS SCIEX API 3000
Interface: TurbolonSpray (ESI) at 400° C.
Polarity: Positive Ion Q1/Q3 Ions:
    232.3/161.2 for (R)-AV1013 eluting at ~5.4 minutes
    232.3/161.2 for (S)-AV1013 eluting at ~6.6 minutes
    203.2/147.3/161.2 for AV1040 eluting at ~5.2 minutes Analysis of pharmacokinetic parameters was performed for each enantiomer via LC/MS bioanalytics and WinNonlin™ analysis (version 4.0.1; Pharsight Corp., Mountain View, Calif.), commercial software designed for the analysis of PK data. The PK modeling was based on a non-compartmental model with gradual input into the central compartment. Computation of the area under the curve (AUC) was based on the sum of trapezoidal areas for the plotted plasma concentration-time data. AUC and associated parameters were estimated by log-linear regression analysis of the terminal phase.

Plasma concentrations for the two different enantiomers of AV1013 upon dosing a racemic mixture of AV1013 to rats is shown in FIG. 1. As evident from the graph, a strong in vivo preference for the S-enantiomer is observed upon dosing racemic AV1013 in rats. This preference results in significantly higher plasma concentrations of the (S)-enantiomer versus the (R)-enantiomer. See Table 1 below.

TABLE 1

RAT PHARMACOKINETICS BASED UPON DOSING OF AV1013 RACEMATE

|  | (S)-AV1013 | (R)-AV1013 |
|---|---|---|
| Cmax (ug/mL) | 1.26 | 0.19 |
| AUC last (ug*hr/mL) | 5.95 | 0.34 |

Figure 2:
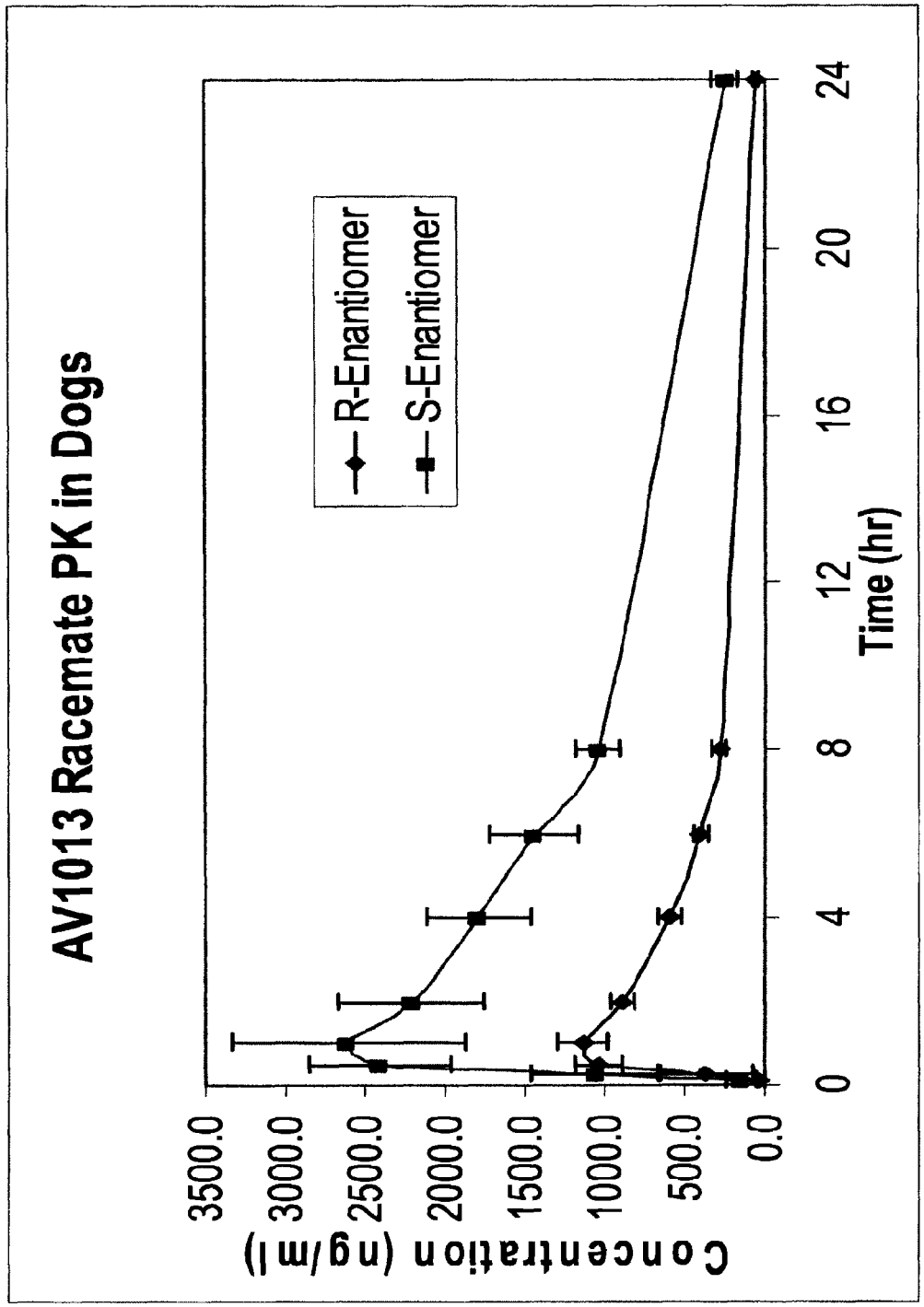
FIG. 2 is a graph illustrating plasma concentrations of each of (R)-AV1013 and (S)-AV1013 upon dosing racemic AV1013 orally in dogs as described in Example 2. AV1013S is predominant.

A similar preference for the (S)-enantiomer, although to a lesser extent, was observed when dogs were dosed with racemic AV1013 as illustrated in FIG. 2 and described in Table 2 below. Analysis of the plasma samples was carried out using a validated enantio-specific bioanalytical method. Exemplary of such a bioanalytical technique is liquid chromatography coupled to tandem mass spectrometry (MS/MS) for detection (i.e., LC/MS/MS).

TABLE 2

DOG PHARMACOKINETICS BASED UPON DOSING OF AV1013 RACEMATE

|  | Dog PK Parameters | |
|---|---|---|
|  | (S)-AV1013 | (R)-AV1013 |
| Cmax (ug/ml) | 2.63 | 1.14 |
| AUC last (ug*hr/ml) | 24.23 | 7.64 |

Example 3

Evaluation of Isolated Enantiomers of AV1013 in a Rat Chronic Constriction Injury Model of Neuropathic Pain The (S)- and the (R)-enantiomer of AV1013 were each evaluated in a rat chronic constriction injury model of neuropathic pain (see, Ledeboer et. al., Neuron Glia Biology, (2006), p 279-291), to determine whether differences in their activity could be observed.

To induce allodynia, male Sprague-Dawley rats underwent chronic constriction injury (CCI) to the sciatic nerve as described by Bennett and Xie, Pain 1988; 33(1):87-107. The plantar surface of the hind paws was stimulated with von Frey filaments (Stoelting) to induce a withdrawal response by blinded personnel. The bending force of fiber required to induce a 50% withdrawal response was calculated following CCI surgery (pre-dosing baseline).

Allodynic rats (N=5-6), received an oral administration of (S)-AV1013 (25 mg/kg), AV1013-R (100 mg/kg) or vehicle. Two hours post-dosing, 50% paw withdrawal threshold was determined by blinded testers using von Frey filaments. The 50% withdrawal threshold prior to CCI surgery, pre-dosing (10 days post-surgery), and 2 hours post-dosing are plotted in FIG. 3.

The data plotted in FIG. 3 demonstrates that the (S)-enantiomer is more potent in vivo than is the (R)-enantiomer. The disparity in improvement of mechanical allodynia observed in rats following administration of individual enantiomers is potentially attributed to higher plasma exposures of S versus R as described in Example 2.

It was also determined that dosing of isolated (S)-enantiomer (99% enantiomeric excess) in rats does not result in detectable levels of the (R)-enantiomer (LLOQ=5 ng/mL). This observation indicates that no detectable inter-conversion of the enantiomers occurs in viva Furthermore, no racemization has been documented in dosing solutions (saline vehicle), or in solvents used for making the bioanalytical solutions (DMSO:methanol, 1:1).

Example 4

Evaluation of (S)-AV1013 in an Inflammatory Pain Model

The (S)-enantiomer of AV1013 was evaluated in an inflammatory pain model (formalin paw model) in mice to assess its analgesic/anti-inflammatory activity.

The model employed is described in detail by Wheeler-Aceto et al (*Psychopharmacology,* 104, p 35-44, (1991)). Briefly, mice were given an intraplantar injection of 5% formalin (25 µl) into the posterior left paw. This treatment induced paw licking in control animals. Mice were briefly observed at 1 minute intervals between 15 and 50 minutes after the injection of formalin and the number of times mice were observed licking the injected paw was recorded. 10 mice were studied in each group. The test was performed blind.

AV1013-S was evaluated at 3 doses (10, 25 and 50 mg/kg), administered p.o. 60 minutes before the test (i.e. 45 minutes before formalin), and compared with a vehicle control group. Gabapentin (300 mg/kg p.o.), administered under the same experimental conditions, was used as reference substance. The experiment therefore included 5 groups.

Data were analyzed by comparing treated groups with vehicle control using unpaired Mann-Whitney U tests. Results are presented in Table 3.

TABLE 3

| TREATMENT (mg/kg) p.o. 60 min before the test (i.e. 45 min before formalin) | Licking Score (Mean +/− SEM) | % Change from Control |
|---|---|---|
| Saline | 15.6 +/− 1.6 | — |
| (S)-AV1013 (10) | 13.1 +/− 1.5 | −16% |
| (S)-AV1013 (25) | 13.1 +/− 1.8 | −16% |
| (S)-AV1013- (50) | 8.6 +/− 1.4 * | −45% |
| Gabapentin (300) | 2.6 +/− 0.8 * | −83% |

Mann-Whitney U test: NS = Not Significant;
* = p < 0.01

As can be seen from the above data, (S)-AV1013 demonstrated analgesic/anti-inflammatory activity in a standard mouse formalin paw model (late-phase). A single oral dose of 50 mg/kg (S)-AV1013 was capable of reducing the number of incidences of paw licking in mice following intraplantar injection of formalin into the paw.

Example 5

Evaluation of (S)-AV1013 in an a Rat Morphine Withdrawal Model

The ability of (S)-AV1013 to reduce/ameliorate withdrawal behavior relative to a control was evaluated in rats. The study was conducted in accordance with the method disclosed by Hutchinson et. al., Brain Behavior and Immunity, V. 23, (2009), p 240-250.

Rats were administered morphine in escalating doses over a five day period to induce dependence (15-22.5 mg/kg/day). (S)-AV1013 (25 mg/kg PO QD) or vehicle (saline) administration was initiated two days prior and continued concomitant with the morphine dosing regimen for a total of 7-days. On day seven all animals were administered naloxone SC to precipitate withdrawal symptoms. Specific withdrawal behaviors were scored over 6×, 10 minute intervals. A total of 15 rats per group were evaluated.

Rats that had been administered (S)-AV1013 displayed reduced withdrawal behaviors (e.g., jumping, rearing, wet-dog shakes, grooming, teeth chattering, ptosis, fidgeting, etc.) relative to those receiving vehicle. (S)-AV1013 attenuated several classic symptoms of withdrawal behavior, but not all. These results are summarized graphically in FIG. 4.

Example 6

Antagonism of Macrophage Migration Inhibitory Factor (MIF) Activity by (S)-AV1013 and (R) AV1013

MIF is a pro-inflammatory cytokine involved in regulating macrophage function and, thus, is implicated in multiple inflammatory diseases. The ability of both (S)-AV1013 and (R)-AV1013 to antagonize MIF-induced macrophage migration was evaluated in an effort to assess its anti-inflammatory activity as follows.

The chemo attractant activities of rhMIF (recombinant human Macrophage migration Inhibitory Factor) and the effect of inhibitors were measured using human peripheral blood monocytes (PBMCs) isolated from whole blood by centrifugation on Histopaque-1077 (Sigma). The cells were washed in RPMI-1640, diluted to $1 \times 10^6$ cells/ml and analyzed immediately. These assays were carried out in 24 well tissue culture plates utilizing 8.0 μm cell culture inserts (Falcon). Recombinant hMIF (90 nM), diluted in RPMI was placed in the cells of a 24 well plate with or without inhibitor (10-fold molar excess or dilution series) and allowed to incubate for 30 min at 37° C., 5% $CO_2$. Washed human monocytes were added to the upper chamber of 8.0 μm cell culture inserts and allowed to incubate for 3 hrs at 37° C., 5% $CO_2$. Cells that migrate through the membrane were fixed in methanol and stained with Geimsa, prior to cell counting using light microscopy.

Results are expressed as the mean number of cells counted per high power field for each of two replicates to obtain statistically significant data. (Legend: –Star=no human MIF, Skull=no human MIF+10 uM (S)-AV1013. See FIGS. 5A and 5B.

As can be seen, both (R)-AV1013 and (S)-AV1013 antagonize MIF-induced macrophage migration in a dose-dependent fashion.

Example 7

Deprotection of (R)-AV1013 Recovery of Optically Product

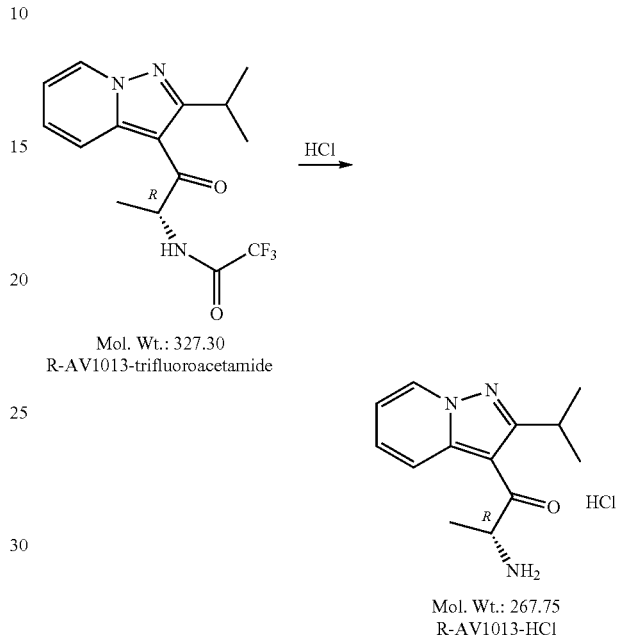

Mol. Wt.: 327.30
R-AV1013-trifluoroacetamide

Mol. Wt.: 267.75
R-AV1013-HCl

As described above, the trifluoroacetamide was the preferred protecting group during the synthesis of (S)-AV1013. The present inventors undertook a study using (R)-AV1013 to evaluate conditions suitable for removal of the trifluoroacetamide group from the desired (S)-enantiomer In particular, the efficiency of removal and the extent of interconversion of the (R)-enantiomer to the (S)-enantiomer during deprotection was assessed for each experimental condition tried.

Thus, stirring (R)-AV1013-COCF$_3$ (0.1% S, 981 mg) with 10 volumes of 6N HCl, at 50° C. for about 29 hours, followed by refrigeration for 5 days and subsequent heating at 50° C. for 5 h resulted in almost quantitative removal of the trifluroacetamide group as indicated by HPLC analysis of the reaction mixture. Chiral analysis of the deprotected product showed that the obtained product had greater than 96% of the (R)-enantiomer. For example, HPLC analysis indicated 92.6% product (P), 1.6% starting material (SM), and 4.5% (S)-enantiomer. The run time was 9.1 min. The crude product was dried under reduced pressure followed by removal of water by azeotropic distillation (3×) following addition of iso-propanol to yield an oil. Crude yield: 109%; Chiral: 96% R, 3.0% S.

The product was purified by recrystallization using a mixture containing 10 volumes ethyl alcohol: 5 volumes iso-propanol. Yield: 0.34 g (42%) with ~100% chemical purity as confirmed by HPLC. The chiral purity was unchanged, and was determined to be about 96% (R)-enantiomer and about 4% (S)-enantiomer.

Improved optical purity was explored by recrystallization of the recovered mother liquors using iso-propanol (IPA)/methyl-tert-butyl ether (MTBE). Direct crystallization by combining IPA and MTBE at 50° C. followed by cooling gradually to room temperature provided an oily mixture that formed a thick paste. In an alternate approach, crystallization was performed by charging 5 volumes of IPA at 50° C., followed by slow addition of 5 volume of MTBE at 50° C. As a result, a hazy-oil mixture was formed. Slow cooling to room temperature resulted in solids formation. Further addition of 5 volume of MTBE resulted in formation of a white slurry. Overnight cooling in the refrigerator followed by isolation of solids and washing with IPA:MTBE resulted in 88 mg of chemically pure (R)-AV1013 HCl with a 100% AUC and, more importantly, 100% optical purity.

Example 8

Alternative Syntheses of ±AV1013

Alternative approaches to chiral (S)-AV1013 were explored as shown in FIG. 7.

A. Desmethylibudilast (Normethylibudilast, AV1001)

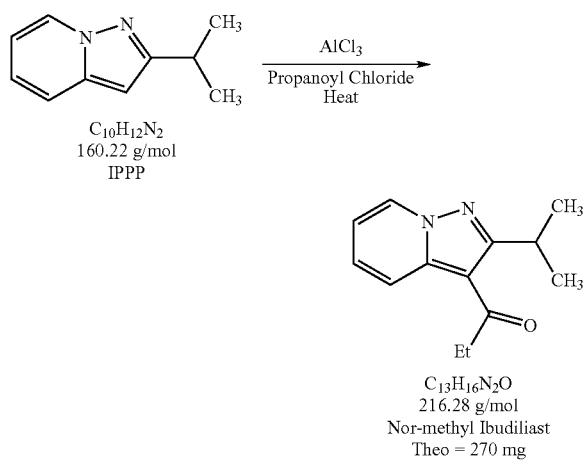

In the reaction shown above, 50 g IPPP was combined with 4 equivalents of $AlCl_3$, 1.5 equivalents propanoyl chloride, and 5 volumes dichloroethane, and the resulting solution stirred at room temperature for 17 hours. Following extraction using water, the organic layer was dried and the solvent removed under reduced pressure to obtain 65.93 g nor-Methyl ibudilast (97.7% yield, dark amber yellow oil. HPLC: AUC=99.7% ( . . . ? . . . ); $^1$H-NMR (d$_6$-DMSO): Clean and conforms to desired product.

B. α-Oximinoketone C

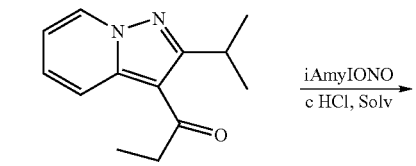

Chemical Formula: $C_{13}H_{16}N_2O$
Molecular Weight: 216.28
C, 72.19; H, 7.46; N, 12.95; O, 7.40
Nor-methylibudilast
B

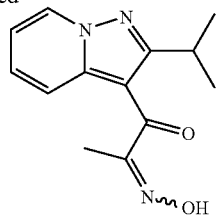

Chemical Formula: $C_{13}H_{15}N_3O_2$
Molecular Weight: 245.28
C, 63.66; H, 6.16; N, 17.13; O, 13.05
alpha-Oximinoketone
C To 15.0 g nor-methylibudilast in methyl-tert-butyl ether (MTBE) was added iso-amyl nitrite. The reaction mixture was stirred at room temperature for 20 hours, following which HPLC analysis indicated the complete absence of nor-methylibudilast. Analysis: HPLC—0% nor-methylibudilast, 78% α-oximinoketone (7.0 min), 8.1% 9.0 min impurity and 0.4% 15.8 min impurity.

The crude product was extracted with MTBE/1N HCl, followed by drying under reduced pressure to yield a purple oil. The oil was further purified by silica gel column chromatography using 1:1 ethyl alcohol:heptane as eluent. Fractions were collected and analyzed for product using thin layer chromatography. Fractions containing the desired product were pooled and the solvent removed under reduced pressure to give an orange solid. 78.5% crude yield of wet orange solid product. Yield following drying of solid 85.2% oxime-ketone, percent purity greater than 88%. The product was not further purified.

C. Conversion of α-Oximinoketone C to (+/−)-AV1013.HCl by Hydrogenolysis using Palladium-Carbon as the Catalyst

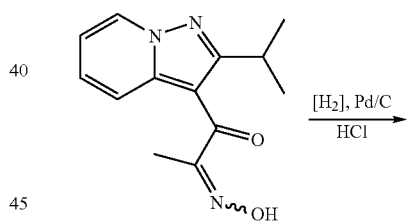

Chemical Formula: $C_{13}H_{15}N_3O_2$
Molecular Weight: 245.28
C, 63.66; H, 6.16; N, 17.13; O, 13.05
alpha-Oximinoketone
C

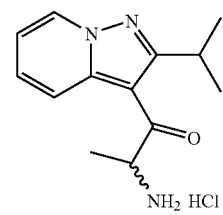

Chemical Formula: $C_{13}H_{17}N_3O$
Molecular Weight 231.29
C, 67.51; H, 7.41; N, 18.17; O, 6.92
Analytical for free base
± AV1013 Salt To 0.5 g α-oximinoketone was added 10 volumes of ethanol and 10 wt % of 10% Pd/C. To this solution were added 2 equivalents of aqueous HCl. After five hours at room temperature the reaction was stopped and analyzed by HPLC. Yield: 26.4% AV1013, 42.3% α-oximinoketone unreacted starting material.

D. Conversion of α-Oximinoketone C to (+/−)-AV1013.HCl by Dithionite Reduction

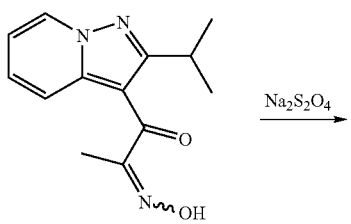

Chemical Formula: $C_{13}H_{15}N_3O_2$
Molecular Weight: 245.28
C, 63.66; H, 6.16; N, 17.13; O, 13.05
alpha-Oximinoketone
C

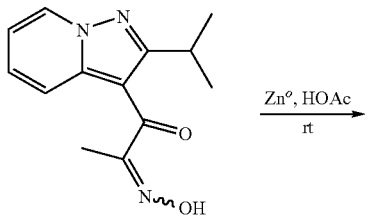

Chemical Formula: $C_{13}H_{17}N_3O$
Molecular Weight 231.29
C, 67.51; H, 7.41; N, 18.17; O, 6.92
± AV1013

The above reaction was carried out using 0.5 g α-oximinoketone starting material, 10 volumes THF, 10 volumes water, 6 equivalents $Na_2S_2O_4$. After 23 hours at ambient temperature, HPLC analysis showed 43.7% AV1013, 1.5% oxime-ketone, 29.4% (4.2 min), impurity (HPLC).

The above reaction was carried out at the same scale but using 10 volumes of acetic acid rather than THF as solvent. After 3 hours at ambient conditions, HPLC analysis showed 57.2% AV1013, 0% α-oximinoketone, 31.9% (4.2 min), impurity.

Alternative reaction conditions were also explored, with crude yields of product ranging from approximately 5% to 52%.

E. Conversion of α-Oximinoketone C to (+/−)-AV1013.HCl by Zinc/Acid Reduction

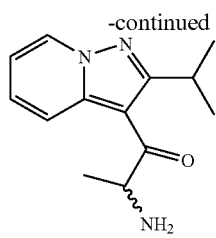

Chemical Formula: $C_{13}H_{15}N_3O_2$
Molecular Weight: 245.28
C, 63.66; H, 6.16; N, 17.13; O, 13.05
alpha-Oximinoketone
C

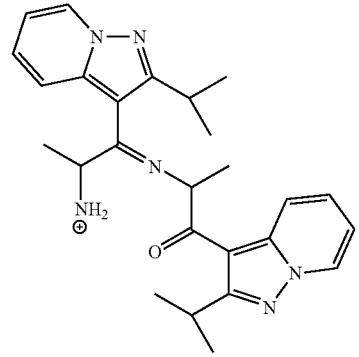

Chemical Formula: $C_{13}H_{17}N_3O$
Molecular Weight 231.29
C, 67.51; H, 7.41; N, 18.17; O, 6.92
± AV1013

Chemical Formula: $C_{26}H_{33}N_6O^+$
Exact Mass: 445.27

Conversion of α-oximinoketone C to racemic AV1013 via zinc-acid reduction was carried out as illustrated above.

Briefly, 83 mg (0.33 mmol) of α-oximinoketone C was treated with 6 equivalents of zinc dust and 6 equivalents of $NH_4OAc$. Ammonium acetate was used rather than acetic acid to enhance reaction rate and suppress self-condensation of the starting oximinoketone. Accordingly, at regular intervals of time, aliquots (supernatant only), were removed for monitoring the progress of reduction. The aliquot at 1 h showed no trace of starting material or self-condensation product. The reaction was quenched, therefore at 1 hour by the addition of aqueous HCl followed by neutralization using sodium hydroxide and extraction with ethyl alcohol. HPLC analysis of the extracted mixture indicated no self-condensation product, but did reveal 10% starting material. AUC of the isolated oil was 83%. MS (fusion) m/e 232 (M+1) and 161 loss of side chain supports the assigned structure.

The oil obtained above was redissolved in ethyl alcohol and treated with 4N HCl in dioxane. The white solid obtained (37 mg) was filtered. HPLC shows amine product at 2.5 min (C, 90%) and broad signal at 9.1 min (10.6%).

F. Preparation of Nor-Methylibudilast Oxime D.

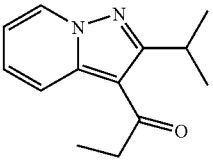

Chemical Formula: $C_{13}H_{16}N_2O$
Molecular Weight: 216.28
C, 72.19; H, 7.46; N, 12.95; O, 7.40
Nor-methylibudilast
B -continued

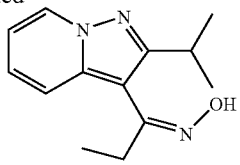

Chemical Formula: $C_{13}H_{17}N_3O$
Molecular Weight: 231.29
C, 67.51; H, 7.41; N, 18.17; O, 6.92
Nor-methylibudilast Oxime
D Oxime D was prepared by conversion of nor-methylibudilast in accordance with the reaction shown schematically above. The reaction was conducted using 15.0 g nor-methylibudilast as the starting material using 15 volumes pyridine and 5.4 equivalents of hydroxylamine hydrochloride under ambient conditions. The reaction was complete in 20 hours. HPLC—0.3% nor-methylibudilast, 91% oxime (6.9 and 7.9 min), 7.3% 15.8 min impurity.

After removal of the solvent under reduced pressure, the crude reaction mixture was dissolved in dichloromethane and extracted with saturated $NaHCO_3$. The combined extracts were dried under vacuum to provide a yellow solid (94.8% crude yield; 92.6% nor-methylibudilast oxime (6.9 and 7.9 min), 0% nor-methylibudilast, 5% 15.8 min impurity. Recrystallization of crude product from solvent mixture containing 5 volumes ethanol and 5 volumes water gave oxime (D). The yield of pure oxime (D) was 29%.

Many modifications and other embodiments will come to mind to one skilled in the art to which this disclosure pertains having the benefit of the teachings presented in the foregoing description. Therefore, it is to be understood that the disclosure is not to be limited to the specific embodiments disclosed and that modifications and other embodiments are intended to be included within the scope of the teachings herein. Although specific terms are employed herein, they are used in a generic and descriptive sense only and not for purposes of limitation.

What is claimed is:

1. A compound (S)-2-amino-1-(2-isopropylpyrazolo[1,5-a]pyridin-3-yl)propan-1-one, a pharmaceutically acceptable salt or a prodrug thereof.

2. The compound of claim 1, wherein the compound is substantially free of its (R)-enantiomer.

3. The compound of claim 1, wherein the enantiomeric purity of the compound is in the range from at least about 94% to at least about 99% purity.

4. The compound of claim 1, wherein the enantiomeric purity of the compound is at least about 99%.

5. The compound of claim 1, wherein the compound is (S)-2-amino-1-(2-isopropylpyrazolo[1,5-a]pyridin-3-yl)propan-1-one hydrochloride.

6. A pharmaceutical composition comprising the compound of claim 1, and a pharmaceutically acceptable carrier.

7. A method for treating neuropathic pain in a subject, comprising administering to the subject a therapeutically effective amount of (S)-2-amino-1-(2-isopropylpyrazolo[1,5-a]pyridin-3-yl)propan-1-one, or a pharmaceutically acceptable salt thereof.

8. The method of claim 7, wherein the neuropathic pain is associated with syndromes selected from the group consisting of viral neuralgias, diabetic neuropathy, phantom limb pain, stump/neuroma pain, post-ischemic pain (stroke), fibromyalgia, reflex sympathetic dystrophy, complex regional pain syndrome, cancer pain, vertebral disk rupture, spinal cord injury, trigeminal neuralgia, cancer-chemotherapy-induced neuropathic pain, and migraine.

9. A method for treating an opioid withdrawal syndrome in a subject, comprising administering to the subject a therapeutically effective amount of (S)-2-amino-1-(2-isopropylpyrazolo[1,5-a]pyridin-3-yl)propan-1-one, or a pharmaceutically acceptable salt thereof.

* * * * *